United States Patent
Ippolito et al.

(10) Patent No.: US 11,911,177 B2
(45) Date of Patent: Feb. 27, 2024

(54) DETERMINING AN EFFICACY OF A TREATMENT PROGRAM

(71) Applicant: Medtronic, Inc., Minneapolis, MN (US)

(72) Inventors: Ekaterina M. Ippolito, Shoreview, MN (US); Shantanu Sarkar, Roseville, MN (US); Eduardo N. Warman, Maple Grove, MN (US); Joel R. Lauer, Clearwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 420 days.

(21) Appl. No.: 16/918,555

(22) Filed: Jul. 1, 2020

(65) Prior Publication Data

US 2022/0000421 A1 Jan. 6, 2022

(51) Int. Cl.
*A61B 5/00* (2006.01)
*G16H 40/60* (2018.01)
(Continued)

(52) U.S. Cl.
CPC .......... *A61B 5/4848* (2013.01); *A61B 5/0205* (2013.01); *A61B 5/4842* (2013.01);
(Continued)

(58) Field of Classification Search
CPC .... A61B 5/4848; A61B 5/4842; A61B 5/7275
See application file for complete search history.

(56) References Cited

U.S. PATENT DOCUMENTS 8,255,046 B2 * 8/2012 Sarkar ............... A61N 1/36521
600/509
8,376,943 B2 2/2013 Kovach et al.
(Continued)

FOREIGN PATENT DOCUMENTS

EP 1491234 B1 2/2008

OTHER PUBLICATIONS

International Search Report and Written Opinion of International Application No. PCT/US2021/041208, dated Oct. 8, 2021, 11 pp.
(Continued)

*Primary Examiner* — Allen Porter
*Assistant Examiner* — Laura Hodge
(74) *Attorney, Agent, or Firm* — Shumaker & Sieffert, P.A.

(57) ABSTRACT

This disclosure is directed to devices, systems, and techniques for determining an efficacy of a treatment program. For example, a medical device system includes a medical device including one or more sensors configured to generate a signal that indicates a parameter of a patient. Additionally, the medical device system includes processing circuitry configured to receive data indicative of a user selection of a reference time; determine a plurality of parameter values of the parameter based on a portion of the signal corresponding to a period of time including the reference time. Additionally, the processing circuitry is configured to identify, based on a first set of parameter values, a reference parameter value, calculate a parameter change value, and determine, based on the parameter change value, whether an improvement or a worsening of the patient has occurred responsive to a treatment administered beginning at the reference time.

19 Claims, 15 Drawing Sheets

(51) Int. Cl.
  *A61B 5/0205* (2006.01)
  *A61B 5/361* (2021.01)
  *A61B 5/024* (2006.01)
  *A61B 5/053* (2021.01)
  *A61B 5/08* (2006.01)
(52) U.S. Cl.
  CPC ............ *A61B 5/686* (2013.01); *A61B 5/7275* (2013.01); *G16H 40/60* (2018.01); *A61B 5/024* (2013.01); *A61B 5/053* (2013.01); *A61B 5/0816* (2013.01); *A61B 5/361* (2021.01)

(56) References Cited

U.S. PATENT DOCUMENTS

| | | |
|---|---|---|
| 9,339,231 B2 | 5/2016 | Thakur et al. |
| 9,770,584 B2 | 2/2017 | Thakur et al. |
| 9,610,445 B2 | 4/2017 | Thakur et al. |
| 10,368,774 B2 | 8/2019 | Sharma et al. |
| 2005/0021091 A1 | 1/2005 | Laske et al. |
| 2010/0030293 A1* | 2/2010 | Sarkar .................... A61B 5/021 607/18 |
| 2011/0144508 A1 | 6/2011 | Blomqvist et al. |
| 2012/0095520 A1* | 4/2012 | Zhang .................... A61B 5/287 607/15 |
| 2017/0246460 A1 | 8/2017 | Ghosh |
| 2017/0246461 A1 | 8/2017 | Ghosh |
| 2017/0303840 A1 | 10/2017 | Stadler et al. |
| 2018/0035898 A1* | 2/2018 | Gunderson ............ A61B 5/287 |
| 2018/0035956 A1* | 2/2018 | Gunderson .......... A61B 5/6882 |
| 2018/0168460 A1* | 6/2018 | Morris ................ A61B 5/6882 |
| 2019/0060656 A1* | 2/2019 | Scott .................... A61N 1/0531 |
| 2019/0083030 A1 | 3/2019 | Thakur et al. |
| 2019/0269926 A1 | 9/2019 | Ghosh |
| 2019/0329043 A1 | 10/2019 | Sharma |
| 2019/0366106 A1 | 12/2019 | Ghosh et al. |

OTHER PUBLICATIONS

Rickard et al., "The ECG Belt for CRT response trial: Design and clinical protocol," PACE—Pacing and Clinical Electrophysiology, vol. 43, No. 10, Jun. 14, 2020, pp. 1063-1071.

* cited by examiner

DETERMINING AN EFFICACY OF A TREATMENT PROGRAM

TECHNICAL FIELD

The disclosure relates generally to medical device systems and, more particularly, medical device systems configured to monitor patient parameters.

BACKGROUND

Some types of medical devices may be used to monitor one or more physiological parameters of a patient. Such medical devices may include, or may be part of a system that includes, sensors that detect signals associated with such physiological parameters. Values determined based on such signals may be used to assist in detecting changes in patient conditions, in evaluating the efficacy of a therapy, or in generally evaluating patient health.

SUMMARY

In general, the disclosure is directed to devices, systems, and techniques for determining whether an improvement or a worsening of one or more symptoms or physiological parameters has occurred in a patient responsive to an administered treatment. For example, a medical device, e.g., an implantable medical device (IMD), may collect a signal which includes one or more values of a parameter (e.g., a physiological parameter) of a patient for a period of time before a treatment is administered and one or more values of the parameter for a period of time after a treatment is administered. Based on the signal, processing circuitry may identify if a change in the parameter, e.g., an improvement or a worsening of the parameter, exists from the period of time before the treatment is administered to the period of time after the treatment is administered. For example, the processing circuitry may determine that an improvement (e.g., a recovery) of the physiological parameter has occurred if a parameter change value is greater than a first threshold parameter change value. Alternatively, the processing circuitry may determine that a worsening of the physiological parameter has occurred in the patient if the parameter change value is less than a second threshold parameter change value.

The techniques of this disclosure may provide one or more advantages. For example, it may be beneficial for the processing circuitry to receive data indicative of a time (e.g., a day, an hour, or a second) in which a treatment program administered to the patient begins. In some examples, the processing circuitry may receive the data from an external device (e.g., a clinician programmer, a patient programmer, or a mobile device), the data representing a user input of the time in which the treatment program begins. The processing circuitry may save the data to a memory. Additionally, the IMD may collect a plurality of parameter values, where each parameter value of the plurality of parameter values represents a measurement of the parameter at a respective point in time, some points in time being before the time in which the treatment program begins and some points in time being after the time in which the treatment program begins. In this way, the processing circuitry may arrive at a more accurate determination of whether an improvement or a worsening has occurred in the respective physiological parameter based on the plurality of parameter values measured by the IMD and the time in which the treatment program begins as compared with techniques in which a determination of a patient status is made without an indication of a time in which the treatment program begins.

In some examples, a medical device system includes a medical device including one or more sensors configured to generate a signal that indicates a parameter of a patient; and processing circuitry configured to: receive data indicative of a user selection of a reference time; determine a plurality of parameter values of the parameter based on a portion of the signal corresponding to a period of time including the reference time, where each parameter value of the plurality of parameter values represents a measurement of the parameter for a respective time interval during the period of time; identify, based on a first set of parameter values of the plurality of parameter values occurring before the reference time, a reference parameter value; calculate, based on a second set of parameter values of the plurality of parameter values occurring after the reference time and based on the reference parameter value, a parameter change value; and determine, based on the parameter change value, whether an improvement or a worsening of the patient has occurred responsive to a treatment administered beginning at the reference time.

In some examples, a method includes generating, by a medical device including one or more sensors, a signal that indicates a parameter of a patient; receiving, by processing circuitry, data indicative of a user selection of a reference time; determining, by the processing circuitry, a plurality of parameter values of the parameter based on a portion of the signal corresponding to a period of time including the reference time, where each parameter value of the plurality of parameter values represents a measurement of the parameter for a respective time interval during the period of time; identifying, by the processing circuitry based on a first set of parameter values of the plurality of parameter values occurring before the reference time, a reference parameter value; calculating, by the processing circuitry based on a second set of parameter values of the plurality of parameter values occurring after the reference time and based on the reference parameter value, a parameter change value; and determining, by the processing circuitry based on the parameter change value, whether an improvement or a worsening of the patient has occurred responsive to a treatment administered beginning at the reference time.

In some examples, a non-transitory computer-readable medium includes instructions for causing one or more processors to: generate a signal that indicates a parameter of a patient; receive data indicative of a user selection of a reference time; determine a plurality of parameter values of the parameter based on a portion of the signal corresponding to a period of time including the reference time, where each parameter value of the plurality of parameter values represents a measurement of the parameter for a respective time interval during the period of time; identify, based on a first set of parameter values of the plurality of parameter values occurring before the reference time, a reference parameter value; calculate, based on a second set of parameter values of the plurality of parameter values occurring after the reference time and based on the reference parameter value, a parameter change value; and determine, based on the parameter change value, whether an improvement or a worsening of the patient has occurred responsive to a treatment administered beginning at the reference time.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

Like reference characters denote like elements throughout the description and figures.

DETAILED DESCRIPTION

This disclosure describes techniques for measuring signals representative of one or more parameters of a patient. Changes in a patient parameter may be a sign of a change (e.g., an improvement or a worsening) of a patient symptom a patient condition, or a physiological parameter responsive to an event, such as administration of a treatment program to the patient. In some examples, it may be beneficial to track the parameter in response to the time in which the treatment program begins in order to ascertain whether the parameter significantly changes in the time following the administration of the treatment program. More specifically, a significant change of the patient parameter from a period of time before the treatment program begins to a period of time after the treatment program begins may be a sign that one or more symptoms or physiological parameters of the patient have improved or worsened due to the treatment program. Additionally, in some cases, it may be beneficial to track more than one parameter of the patient relative to the time in which the treatment program begins in order to determine whether an improvement or a worsening of the patient has occurred. In some examples, it may be beneficial to track the parameter on a rolling basis in order to ascertain whether the parameter significantly changes in a time (e.g., 7 days) preceding a current time.

Figure 1:
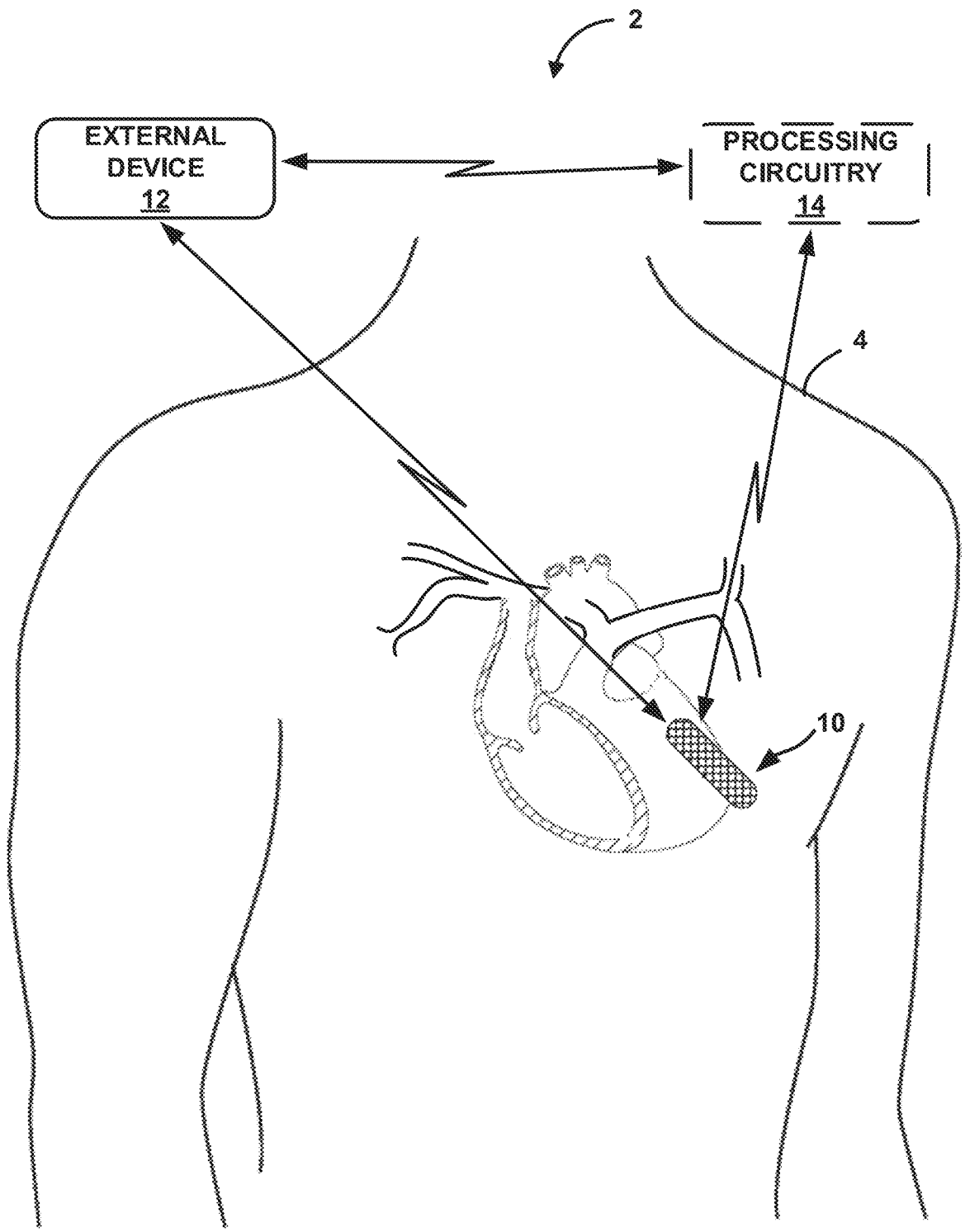
FIG. 1 illustrates the environment of an example medical device system in conjunction with a patient, in accordance with one or more techniques of this disclosure.

FIG. 1 illustrates the environment of an example medical device system 2 in conjunction with a patient 4, in accordance with one or more techniques of this disclosure. The example techniques may be used with an implantable medical device (IMD) 10, which may be in wireless communication with at least one of external device 12, processing circuitry 14, and other devices not pictured in FIG. 1. For example, an external device (not illustrated in FIG. 1) may include at least a portion of processing circuitry 14, the external device configured for communication with IMD 10, and external device 12. In some examples, IMD 10 is implanted outside of a thoracic cavity of patient 4 (e.g., subcutaneously in the pectoral location illustrated in FIG. 1). IMD 10 may be positioned near the sternum near or just below the level of patient 4's heart, e.g., at least partially within the cardiac silhouette. In some examples, IMD 10 takes the form of a LINQ™ Insertable Cardiac Monitor (ICM), available from Medtronic plc, of Dublin, Ireland. The example techniques may additionally, or alternatively, be used with a medical device not illustrated in FIG. 1 such as another type of IMD, a patch monitor device, a wearable device (e.g., smart watch), or another type of external medical device.

Although in one example IMD 10 takes the form of an ICM, in other examples, IMD 10 takes the form of any combination of implantable cardiac devices (ICDs) with intravascular or extravascular leads, pacemakers, cardiac resynchronization therapy devices (CRT-Ds), neuromodulation devices, left ventricular assist devices (LVADs), implantable sensors, cardiac resynchronization therapy pacemakers (CRT-Ps), implantable pulse generators (IPGs), orthopedic devices, or drug pumps, as examples. Moreover, techniques of this disclosure may be used to measure one or more patient parameters based on signals collected by one or more of the aforementioned devices. Additionally, or alternatively, techniques of this disclosure may be used to measure one or more patient parameters based on signals collected by one or more external devices such as patch devices, wearable devices (e.g., smart watches), wearable sensors, or any combination thereof.

Clinicians sometimes diagnose a patient (e.g., patient 4) with medical conditions and/or determine whether a condition of patient 4 is improving or worsening based on one or more observed physiological signals collected by physiological sensors, such as electrodes, optical sensors, chemical sensors, temperature sensors, acoustic sensors, and motion sensors. In some cases, clinicians apply non-invasive sensors to patients in order to sense one or more physiological signals while a patent is in a clinic for a medical appointment. However, in some examples, events that may change a condition of a patient, such as administration of a therapy, may occur outside of the clinic. As such, in these examples, a clinician may be unable to observe the physiological markers needed to determine whether an event has changed a medical condition of the patient and/or determine whether a medical condition of the patient is improving or worsening while monitoring one or more physiological signals of the patient during a medical appointment. In the example illustrated in FIG. 1, IMD 10 is implanted within patient 4 to continuously record one or more physiological signals of patient 4 over an extended period of time.

In some examples, IMD 10 includes a plurality of electrodes. The plurality of electrodes is configured to detect signals that enable processing circuitry of IMD 10 to determine current values of additional parameters associated with the cardiac and/or lung functions of patient 4. In some examples, the plurality of electrodes of IMD 10 are configured to detect a signal indicative of an electric potential of the tissue surrounding the IMD 10. Moreover, IMD 10 may additionally or alternatively include one or more optical sensors, accelerometers, temperature sensors, chemical sensors, light sensors, pressure sensors, and acoustic sensors, in some examples. Such sensors may detect one or more physiological parameters indicative of a patient condition.

External device 12 may be a hand-held computing device with a display viewable by the user and an interface for providing input to external device 12 (e.g., a user input mechanism). For example, external device 12 may include a small display screen (e.g., a liquid crystal display (LCD) or a light emitting diode (LED) display) that presents information to the user. In addition, external device 12 may include a touch screen display, keypad, buttons, a peripheral pointing device, voice activation, or another input mechanism that allows the user to navigate through the user interface of external device 12 and provide input. If external device 12 includes buttons and a keypad, the buttons may be dedicated to performing a certain function, e.g., a power button, the buttons and the keypad may be soft keys that change in function depending upon the section of the user interface currently viewed by the user, or any combination thereof.

In other examples, external device 12 may be a larger workstation or a separate application within another multi-function device, rather than a dedicated computing device. For example, the multi-function device may be a notebook computer, tablet computer, workstation, one or more servers, cellular phone, personal digital assistant, or another computing device that may run an application that enables the computing device to operate as a secure device.

When external device 12 is configured for use by the clinician, external device 12 may be used to transmit instructions to IMD 10. Example instructions may include requests to set electrode combinations for sensing and any other information that may be useful for programming into IMD 10. The clinician may also configure and store operational parameters for IMD 10 within IMD 10 with the aid of external device 12. In some examples, external device 12 assists the clinician in the configuration of IMD 10 by providing a system for identifying potentially beneficial operational parameter values.

Whether external device 12 is configured for clinician or patient use, external device 12 is configured to communicate with IMD 10 and, optionally, another computing device (not illustrated by FIG. 1), via wireless communication. External device 12, for example, may communicate via near-field communication technologies (e.g., inductive coupling, NFC or other communication technologies operable at ranges less than 10-20 cm) and far-field communication technologies (e.g., RF telemetry according to the 802.11 or Bluetooth® specification sets, or other communication technologies operable at ranges greater than near-field communication technologies). In some examples, external device 12 is configured to communicate with a computer network, such as the Medtronic CareLink® Network developed by Medtronic, plc, of Dublin, Ireland. For example, external device 12 may send data, such as data received from IMD 10, to another external device such as a smartphone, a tablet, or a desktop computer, and the other external device may in turn send the data to the computer network. In other examples, external device 12 may directly communicate with the computer network without an intermediary device.

Processing circuitry 14, in some examples, may include one or more processors that are configured to implement functionality and/or process instructions for execution within IMD 10. For example, processing circuitry 14 may be capable of processing instructions stored in a storage device. Processing circuitry 14 may include, for example, microprocessors, digital signal processors (DSPs), application specific integrated circuits (ASICs), field-programmable gate arrays (FPGAs), or equivalent discrete or integrated logic circuitry, or a combination of any of the foregoing devices or circuitry. Accordingly, processing circuitry 14 may include any suitable structure, whether in hardware, software, firmware, or any combination thereof, to perform the functions ascribed herein to processing circuitry 14.

Processing circuitry 14 may represent processing circuitry located within any one or both of IMD 10 and external device 12. In some examples, processing circuitry 14 may be entirely located within a housing of IMD 10. In other examples, processing circuitry 14 may be entirely located within a housing of external device 12. In other examples, processing circuitry 14 may be located within any one or combination of IMD 10, external device 12, and another device or group of devices that are not illustrated in FIG. 1. As such, techniques and capabilities attributed herein to processing circuitry 14 may be attributed to any combination of IMD 10, external device 12, and other devices that are not illustrated in FIG. 1.

Medical device system 2 of FIG. 1 is an example of a system configured to collect an electrogram (EGM) signal according to one or more techniques of this disclosure. In some examples, processing circuitry 14 includes EGM analysis circuitry configured to determine one or more parameters of an EGM signal of patient 4. In one example, an EGM signal is sensed via one or more electrodes of IMD 10. An EGM is a signal representative of electrical activity of the heart, measured by electrodes implanted within the body, and often within the heart itself. For example, a cardiac EGM may include P-waves (depolarization of the atria), R-waves (depolarization of the ventricles), and T-waves (repolarization of the ventricles), among other events. Information relating to the aforementioned events, such as time separating one or more of the events, may be applied for a number of purposes, such as to determine whether an arrhythmia is occurring and/or predict whether an arrhythmia is likely to occur. Cardiac signal analysis circuitry, which may be implemented as part of processing circuitry 14, may perform signal processing techniques to extract information indicating the one or more parameters of the cardiac signal.

In some examples, IMD 10 includes one or more accelerometers. An accelerometer of IMD 10 may collect an accelerometer signal which reflects a measurement of any one or more of a motion of patient 4, a posture of patient 4 and a body angle of patient 4. In some cases, the accelerometer may collect a three-axis accelerometer signal indicative of patient 4's movements within a three-dimensional Cartesian space. For example, the accelerometer signal may include a vertical axis accelerometer signal vector, a lateral axis accelerometer signal vector, and a frontal axis accelerometer signal vector. The vertical axis accelerometer signal vector may represent an acceleration of patient 4 along a vertical axis, the lateral axis accelerometer signal vector may represent an acceleration of patient 4 along a lateral axis, and the frontal axis accelerometer signal vector may represent an acceleration of patient 4 along a frontal axis. In some cases, the vertical axis substantially extends along a torso of patient 4 when patient 4 from a neck of patient 4 to a waist of patient 4, the lateral axis extends across a chest of patient 4 perpendicular to the vertical axis, and the frontal axis extends outward from and through the chest of patient 4, the frontal axis being perpendicular to the vertical axis and the lateral axis.

IMD 10 may measure a set of parameters including an impedance (e.g., subcutaneous impedance, an intrathoracic impedance or an intracardiac impedance) of patient 4, a respiratory rate of patient 4 during night hours, a respiratory rate of patient 4 during day hours, a heart rate of patient 4 during night hours, a heart rate of patient 4 during day hours, an atrial fibrillation (AF) burden of patient 4, a ventricular rate of patient 4 while patient 4 is experiencing AF, or any combination thereof. Processing circuitry 14 may analyze any one or more of the set of parameters in order to determine an efficacy of a treatment program administered to patient 4. In some examples, the treatment program may include treatment delivered by one or more medical devices such as ICDs with intravascular or extravascular leads, pacemakers, CRT-Ds, neuromodulation devices, LVADs, implantable sensors, orthopedic devices, or drug pumps. Additionally, or alternatively, the treatment program may include in-clinic treatments administered by medical professionals, prescribed pharmaceutical regimens, treatments administered by one or more external medical devices, or any combination thereof. In any case, processing circuitry 14 may determine the efficacy of the treatment program by determining a time in which the treatment program is administered (e.g., including a time in which the treatment program begins and/or a time in which the treatment program ends) and analyzing values of any one or combination of the set of parameters relative to the time in which the treatment program is administered. Alternatively, in some examples, processing circuitry 14 may determine the efficacy of a treatment program by evaluating one or more parameters on a rolling basis in order to determine whether the one or more parameters have changed over a period of time.

In some examples, one or more sensors (e.g., electrodes, motion sensors, optical sensors, temperature sensors, or any combination thereof) of IMD 10 may generate a signal that indicates a parameter of a patient. In some examples, the signal that indicates the parameter includes a plurality of parameter values, where each parameter value of the plurality of parameter values represents a measurement of the parameter at a respective interval of time. The plurality of parameter values may represent a sequence of parameter values, where each parameter value of the sequence of parameter values are collected by IMD 10 at a start of each time interval of a sequence of time intervals. For example, IMD 10 may perform a parameter measurement in order to determine a parameter value of the sequence of parameter values according to a recurring time interval (e.g., every day, every night, every other day, every twelve hours, every hour, or any other recurring time interval). In this way, IMD 10 may be configured to track a respective patient parameter more effectively as compared with a technique in which a patient parameter is tracked during patient visits to a clinic, since IMD 10 is implanted within patient 4 and is configured to perform parameter measurements according to recurring time intervals without missing a time interval or performing a parameter measurement off schedule.

Processing circuitry 14 may receive a portion of the signal that includes the plurality of parameter values of the parameter. In this way, processing circuitry 14 may receive at least a portion of the sequence of parameter values such that processing circuitry 14 can analyze the signal in order to determine whether an improvement or a worsening is occurring in patient 4. In some examples, processing circuitry 14 may receive data indicative of a user selection of a reference time. Processing circuitry 14 may receive the data from external device 12 or another device, where the user selection is a patient selection and/or a clinician selection of a time in which a treatment program is administered. As described herein, the "time" in which a treatment program begins may refer to a window of time in which the treatment program is administered, a point of time (e.g., a day, an hour, a second, or a fraction of a second) in which the treatment program begins, a point of time in which the treatment program ends, or any combination thereof. In some examples, the treatment program may be administered in an in-patient medical facility, in an out-patient medical facility, outside of a medical facility (e.g., at a home of the patient), or any combination thereof.

In some examples, IMD 10 may continuously collect parameter values at a predetermined frequency. IMD 10, a server, or another storage device may include a buffer or other memory structure which temporarily or permanently stores parameter values. Responsive to receiving the data indicative of a user selection of the reference time, processing circuitry 14 retrieve or access one or more parameter values for analysis based on the reference time which indicates an event such as a start of a treatment program.

In order to determine whether a treatment program is effective, it may be beneficial for processing circuitry 14 to determine whether a patient parameter reflects an improvement (e.g., a recovery) of patient 4 in relation to aspects of a window of time in which the treatment program is administered, such as a time in which the treatment program begins. Processing circuitry 14 may identify a reference parameter value corresponding to a period of time before the treatment program is administered to patient 4. In this way, processing circuitry 14 may determine a baseline value in which to compare parameter values measured while the treatment program is being administered or after the treatment program concludes.

Processing circuitry 14 may determine whether the patient parameter reflects an improvement of patient 4 based on determining a clinically significant change in a patient parameter relative to an occurrence of an event. The event may include, for example, a start of a treatment program administered to patient, an end of the treatment program administered to patient 4. The clinically significant change may represent either a positive change in the parameter or a negative change in the parameter. As used herein a "start of a treatment program" may refer to a change to an ongoing treatment program (e.g., a change in a medication dosage, a change in one or more parameters of electrical stimulation therapy) and/or a start of a new treatment program.

Processing circuitry 14 may identify, based on a first set of parameter values of the plurality of parameter values, the reference parameter value. For example, processing circuitry 14 may identify the reference parameter value to be a mean or a median of the first set of parameter values. The first set of parameter values may represent parameter values that are collected by IMD 10 prior to the time in which the treatment program begins. In some examples, processing circuitry 14 may select the first set of parameter values based on the time in which the treatment program begins and calculate a "delta value" to be a difference between the reference parameter value and a target parameter value. The target parameter value may represent a parameter value corresponding to a full recovery or a near-full recovery of patient 4 from a symptom or a condition. In other words, if the parameter deviates from the target parameter value due to a condition or a symptom present in patient 4, an improvement of patient 4 may, in some cases, be measured based on a return or a partial return of the parameter to the target parameter value. In this way, the deviation of the parameter from the target parameter value, caused by the condition or the symptom, may be indicated by the reference parameter value. Additionally, in some examples, processing circuitry 14 may be configured to identify a significant worsening of a patient condition or physiological parameter by determining that the parameter has changed from the reference parameter value away from the target parameter value.

Subsequent to identifying the reference parameter value and the delta value, processing circuitry 14 may calculate, based on a second set of parameter values of the plurality of parameter values occurring after the reference time and based on the reference parameter value, a parameter change value. The parameter change value may represent a value which indicates a relative amount that the parameter has changed from the reference parameter value after the treatment program begins. The second set of parameter values may represent parameter values that are collected by IMD 10 after the time in which the treatment program begins. If the parameter change value represents a change towards the target parameter value, processing circuitry may determine that an improvement has occurred in patient 4. If the parameter change value represents a change away from the target parameter value, processing circuitry may determine that a worsening has occurred in patient 4.

In some examples, processing circuitry 14 is configured to select the second set of parameter values. In some examples, to select the second set of parameter values, processing circuitry 14 is configured to select the second set of parameter values based on the time in which the treatment program begins. For example, each parameter value of the plurality of parameter values may be separated by respective neighboring (e.g., consecutive) parameter values of the plurality of parameter values by a window of time having a predetermined duration (e.g., one day). In this way, the plurality of parameter values may form a sequence of parameter values that are collected by IMD 10 at a predetermined frequency (e.g., one parameter value per day, one parameter value per hour, one parameter value per minute, or any other frequency.). In some examples, processing circuitry 14 may receive data indicative of a user selection of the predetermined duration and/or the predetermined frequency. In order to select the second set of parameter values, processing circuitry 14 may select a parameter of the sequence of parameter values which is collected by IMD 10 closest to the time in which the treatment program begins. For example, processing circuitry 14 may receive data indicative of the time in which the treatment program begins. Subsequently, processing circuitry 14 may identify the parameter value of the sequence of parameter values that is collected closest to the time in which the treatment program begins (e.g., the therapy start parameter value). In some examples, processing circuitry 14 may select the second set of parameter values to include a group of, e.g., consecutive, parameter values of the sequence of parameter values that are collected by IMD 10 following the therapy start parameter value.

In some examples, processing circuitry 14 may select the second set of parameter values to include the parameter value of the sequence of parameter values which is located a predetermined number of parameter values, e.g., four parameter values, after the therapy start parameter value. Additionally, processing circuitry 14 may select the second set of parameter values to include the parameter value of the sequence of parameter values which is located five parameter values after the therapy start parameter value, and processing circuitry 14 may select the second set of parameter values to include the parameter value of the sequence of parameter values which is located six parameter values after the therapy start parameter value. In this way, the second set of parameter values may include three consecutive parameter values which start a predetermined number of days (e.g., 5 days) after the start of therapy, but this is not required. In some examples, the second set of parameter values may include a set of less than three consecutive parameter values, a set of more than three consecutive parameter values, or a set of parameter values which include at least two parameter values which are non-consecutive. In some examples, the second set of parameter values may start less than five days after the therapy start parameter value or more than five days (e.g., six days) after the therapy start parameter value.

The second set of parameter values may include any one or more parameter values which are collected by IMD 10 after the therapy start parameter value. Processing circuitry 14 may select the first set of parameter values, much like the second set of parameter values, based on the therapy start parameter value which represents the closest parameter value to the time in which the therapy program begins. For example, processing circuitry 14 may select the first set of parameter values to include the four consecutive parameter values of the sequence of parameter values immediately preceding the therapy start parameter value, but this is not required. Processing circuitry 14 may select the first set of parameter values to include any one or more parameter values of the sequence of parameter values which precede the therapy start parameter value.

To calculate the parameter change value, processing circuitry 14 may be configured to identify a set of difference values. In some examples, processing circuitry 14 may identify each difference value of the set of difference values by calculating a difference between a respective parameter value of the second set of parameter values and the reference parameter value, and processing circuitry 14 may calculate the parameter change value based on the set of difference values. For example, processing circuitry 14 may determine a sum of the set of difference values and processing circuitry 14 may determine the delta value which represents a difference between the reference parameter value and the target parameter value. Processing circuitry 14 may calculate the parameter change value to be a ratio of the sum of the set of difference values to the delta value.

Processing circuitry 14 may determine, based on the parameter change value, whether an improvement or a worsening of the patient has occurred responsive to a treatment administered to patient 4. For example, to determine whether an improvement of patient 4 has occurred, processing circuitry 14 is configured to determine whether the parameter change value exceeds a first threshold parameter change value. If the parameter change value exceeds the first threshold parameter change value, processing circuitry 14 may determine that an improvement (e.g., a recovery) of patient 4 has occurred by the end of the second set of parameter values. As used herein, the term "exceeds" refers to examples in which the parameter change value is greater than a respective threshold when the threshold is a positive value and examples in which the parameter change value is less than a respective threshold when the threshold is negative. If the parameter change value does not exceed the first threshold parameter change value, processing circuitry 14 may determine that the improvement of patient 4 has not occurred by the end of the second set of parameter values. In some examples, the first threshold parameter change value is within a range from 0.5 to 0.9 (e.g., 0.7), but this is not required. The parameter change value may represent any value or range of values.

In some examples, if the parameter change value exceeds a second threshold parameter change value, processing circuitry 14 may determine that a worsening of patient 4 has occurred by the end of the second set of parameter values. In some examples, the first threshold parameter change value and the second parameter change value have opposite signs. That is, the first threshold parameter change value may be positive and the second threshold parameter change value may be negative or the first threshold parameter change value may be negative and the second threshold parameter change value may be positive.

Although processing circuitry 14 is described herein as determining whether an improvement or a worsening of patient 4 has occurred due to a treatment program based on determining whether an improvement or a worsening of a single parameter measured by IMD 10 has occurred, processing circuitry 14 may, in some cases, identify an improvement or a worsening of patient 4 based on more than one parameter collected by IMD 10 and/or other devices not illustrated in FIG. 1. For example, processing circuitry 14 may receive data indicative of a set of sequences of parameter values, where each sequence of parameter values of the set of sequences of parameter values corresponds to a respective parameter of a set of parameters. Processing circuitry 14 may determine, based on a time in which the treatment program begins, whether a an improvement or a worsening is detected in each parameter of the set of parameters. Based on whether processing circuitry detects an improvement or a worsening in each parameter of the set of parameters, processing circuitry 14 may determine whether an improvement or a worsening has occurred in a medical condition of patient 4 due to the therapy program. Additionally, or alternatively, processing circuitry 14 may combine the set of sequences of parameter values into a single set of parameter values which define a combined metric. Processing circuitry 14 may analyze the single set of parameter values which define the combined metric in order to determine whether an improvement or a worsening of a medical condition of patient 4 has occurred.

In some examples, processing circuitry 14 is configured to determine whether an improvement or a worsening of patient 4 has occurred based on one or more parameters in addition to or alternatively to determining the parameter change value and comparing the parameter change value to one or more threshold parameter change values. For example, processing circuitry 14 may analyze a sequence of parameter values by performing one or more operations on the sequence of parameter values, e.g., evaluating rate of change or evaluating features such as slew rate and slope of a diagnostic metric. In some examples, processing circuitry 14 may calculate a derivative of the sequence of parameter values, calculate an integral of the sequence of parameter values, fit the sequence of parameter values to a known curve to evaluate deviation from a normal trajectory, or any combination thereof. Processing circuitry 14 may determine, using any one of these operations, whether an improvement or a worsening of patient 4 has occurred.

In some examples, processing circuitry 14 may calculate the parameter change value to evaluate an efficacy of a diuretic medication using raw diagnostic variables collected by IMD 10, the diagnostic variables including an impedance (e.g., a subcutaneous impedance, an intrathoracic impedance, or an intracardiac impedance), respiratory rate, night heart rate, AF burden, ventricular rate during AF, R-wave amplitude, R-wave width, R-wave slew rate, heart sound amplitudes, tissue perfusion values, tissue temperature values, or any combination thereof, as these diagnostic variables may respond dynamically to patient volume status. In some examples, for each respective diagnostic variable, a reference value may be calculated as the average of the last four days before a start of a treatment program such as a pro re nata (PRN) treatment program. In some examples, a difference between raw values of each respective diagnostic variable at day 5 to 7 after PRN initiation and a target value may be computed in order to determine whether an improvement or a worsening of has occurred in a medical condition of patient 4.

Figure 2:
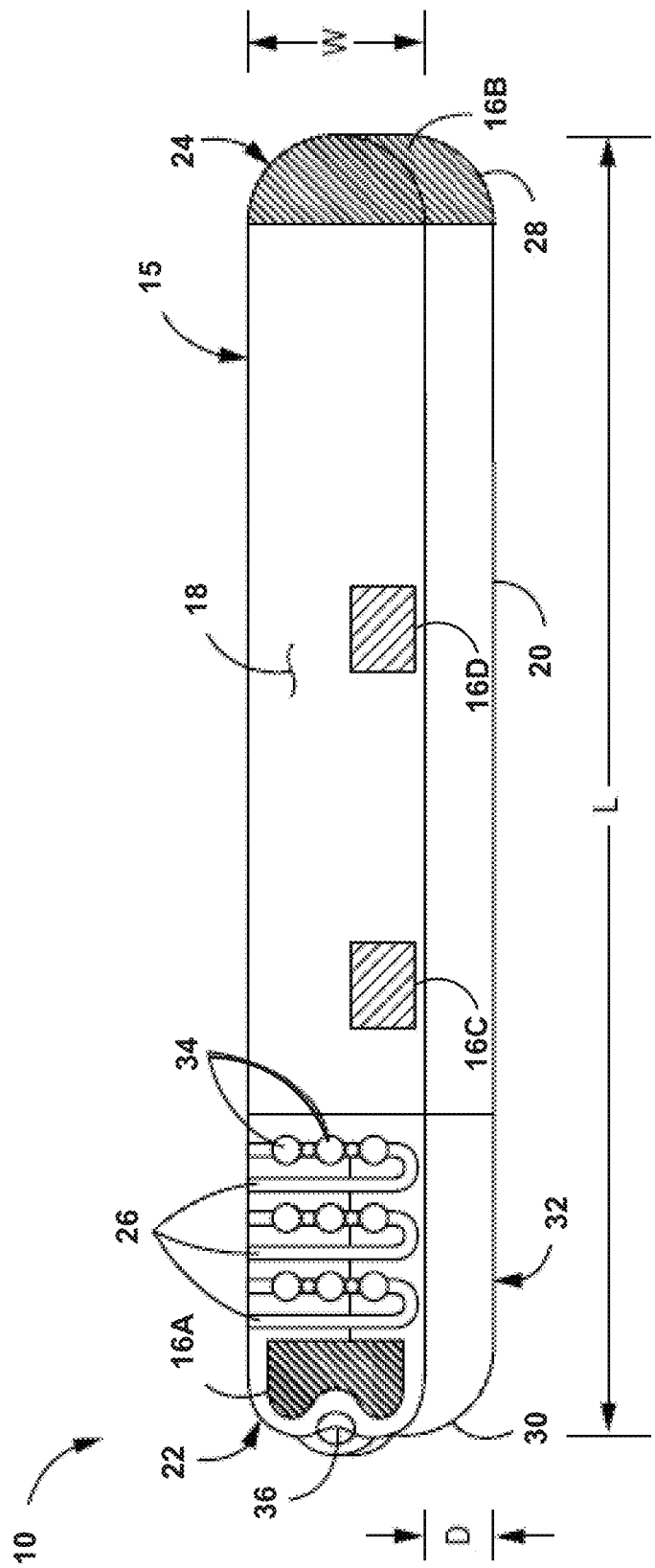
FIG. 2 is a conceptual drawing illustrating an example configuration of the implantable medical device (IMD) of the medical device system of FIG. 1, in accordance with one or more techniques described herein.

FIG. 2 is a conceptual drawing illustrating an example configuration of IMD 10 of the medical device system 2 of FIG. 1, in accordance with one or more techniques described herein. In the example shown in FIG. 2, IMD 10 may include a leadless, subcutaneously-implantable monitoring device having housing 15, proximal electrode 16A, and distal electrode 16B. Housing 15 may further include first major surface 18, second major surface 20, proximal end 22, and distal end 24. In some examples, IMD 10 may include one or more additional electrodes 16C, 16D positioned on one or both of major surfaces 18, 20 of IMD 10. Housing 15 encloses electronic circuitry located inside the IMD 10, and protects the circuitry contained therein from fluids such as body fluids. In some examples, electrical feedthroughs provide electrical connection of electrodes 16A-16D, and antenna 26, to circuitry within housing 15. In some examples, electrode 16B may be formed from an uninsulated portion of conductive housing 15.

In the example shown in FIG. 2, IMD 10 is defined by a length L, a width W, and thickness or depth D. In this example, IMD 10 is in the form of an elongated rectangular prism in which length L is significantly greater than width W, and in which width W is greater than depth D. However, other configurations of IMD 10 are contemplated, such as those in which the relative proportions of length L, width W, and depth D vary from those described and shown in FIG. 2. In some examples, the geometry of the IMD 10, such as the width W being greater than the depth D, may be selected to allow IMD 10 to be inserted under the skin of the patient using a minimally invasive procedure and to remain in the desired orientation during insertion. In addition, IMD 10 may include radial asymmetries (e.g., the rectangular shape)

along a longitudinal axis of IMD 10, which may help maintain the device in a desired orientation following implantation.

In some examples, a spacing between proximal electrode 16A and distal electrode 16B may range from about 30-55 mm, about 35-55 mm, or about 40-55 mm, or more generally from about 25-60 mm. Overall, IMD 10 may have a length L of about 20-30 mm, about 40-60 mm, or about 45-60 mm. In some examples, the width W of major surface 18 may range from about 3-10 mm, and may be any single width or range of widths between about 3-10 mm. In some examples, a depth D of IMD 10 may range from about 2-9 mm. In other examples, the depth D of IMD 10 may range from about 2-5 mm, and may be any single or range of depths from about 2-9 mm. In any such examples, IMD 10 is sufficiently compact to be implanted within the subcutaneous space of patient 4 in the region of a pectoral muscle.

IMD 10, according to an example of the present disclosure, may have a geometry and size designed for ease of implant and patient comfort. Examples of IMD 10 described in this disclosure may have a volume of 3 cubic centimeters ($cm^3$) or less, 1.5 $cm^3$ or less, or any volume therebetween. In addition, in the example shown in FIG. 2, proximal end 22 and distal end 24 are rounded to reduce discomfort and irritation to surrounding tissue once implanted under the skin of patient 4.

In the example shown in FIG. 2, first major surface 18 of IMD 10 faces outward towards the skin, when IMD 10 is inserted within patient 4, whereas second major surface 20 is faces inward toward musculature of patient 4. Thus, first and second major surfaces 18, 20 may face in directions along a sagittal axis of patient 4 (see FIG. 1), and this orientation may be maintained upon implantation due to the dimensions of IMD 10.

Proximal electrode 16A and distal electrode 16B may be used to sense cardiac EGM signals (e.g., electrocardiogram (ECG) signals) when IMD 10 is implanted subcutaneously in patient 4. In some examples, processing circuitry of IMD 10 also may determine whether cardiac ECG signals of patient 4 are indicative of arrhythmia or other abnormalities, which processing circuitry of IMD 10 may evaluate in determining whether a medical condition (e.g., heart failure, sleep apnea, or COPD) of patient 4 has changed. The cardiac ECG signals may be stored in a memory of the IMD 10, and data derived from the cardiac ECG signals may be transmitted via integrated antenna 26 to another medical device, such as external device 12. In some examples, one or both of electrodes 16A and 16B also may be used by IMD 10 to detect impedance values during impedance measurements performed by IMD 10. In some examples, such impedance values detected by IMD 10 may reflect a resistance value associated with a contact between electrodes 16A, 16B, and target tissue of patient 4. Additionally, in some examples, electrodes 16A, 16B may be used by communication circuitry of IMD 10 for tissue conductance communication (TCC) communication with external device 12 or another device.

In the example shown in FIG. 2, proximal electrode 16A is in close proximity to proximal end 22, and distal electrode 16B is in close proximity to distal end 24 of IMD 10. In this example, distal electrode 16B is not limited to a flattened, outward facing surface, but may extend from first major surface 18, around rounded edges 28 or end surface 30, and onto the second major surface 20 in a three-dimensional curved configuration. As illustrated, proximal electrode 16A is located on first major surface 18 and is substantially flat and outward facing. However, in other examples not shown here, proximal electrode 16A and distal electrode 16B both may be configured like proximal electrode 16A shown in FIG. 2, or both may be configured like distal electrode 16B shown in FIG. 2. In some examples, additional electrodes 16C and 16D may be positioned on one or both of first major surface 18 and second major surface 20, such that a total of four electrodes are included on IMD 10. Any of electrodes 16A-16D may be formed of a biocompatible conductive material. For example, any of electrodes 16A-16D may be formed from any of stainless steel, titanium, platinum, iridium, or alloys thereof. In addition, electrodes of IMD 10 may be coated with a material such as titanium nitride or fractal titanium nitride, although other suitable materials and coatings for such electrodes may be used.

In the example shown in FIG. 2, proximal end 22 of IMD 10 includes header assembly 32 having one or more of proximal electrode 16A, integrated antenna 26, anti-migration projections 34, and suture hole 36. Integrated antenna 26 is located on the same major surface (e.g., first major surface 18) as proximal electrode 16A, and may be an integral part of header assembly 32. In other examples, integrated antenna 26 may be formed on the major surface opposite from proximal electrode 16A, or, in still other examples, may be incorporated within housing 15 of IMD 10. Antenna 26 may be configured to transmit or receive electromagnetic signals for communication. For example, antenna 26 may be configured to transmit to or receive signals from a programmer via inductive coupling, electromagnetic coupling, tissue conductance, Near Field Communication (NFC), Radio Frequency Identification (RFID), Bluetooth®, Wi-Fi®, or other proprietary or non-proprietary wireless telemetry communication schemes. Antenna 26 may be coupled to communication circuitry of IMD 10, which may drive antenna 26 to transmit signals to external device 12 and may transmit signals received from external device 12 to processing circuitry of IMD 10 via communication circuitry.

IMD 10 may include several features for retaining IMD 10 in position once subcutaneously implanted in patient 4. For example, as shown in FIG. 2, housing 15 may include anti-migration projections 34 positioned adjacent integrated antenna 26. Anti-migration projections 34 may include a plurality of bumps or protrusions extending away from first major surface 18 and may help prevent longitudinal movement of IMD 10 after implantation in patient 4. In other examples, anti-migration projections 34 may be located on the opposite major surface as proximal electrode 16A and/or integrated antenna 26. In addition, in the example shown in FIG. 2 header assembly 32 includes suture hole 36, which provides another means of securing IMD 10 to the patient to prevent movement following insertion. In the example shown, suture hole 36 is located adjacent to proximal electrode 16A. In some examples, header assembly 32 may include a molded header assembly made from a polymeric or plastic material, which may be integrated or separable from the main portion of IMD 10.

Electrodes 16A and 16B may be used to sense cardiac ECG signals, as described above. Additional electrodes 16C and 16D may be used to sense subcutaneous tissue impedance, in addition to or instead of electrodes 16A, 16B, in some examples. In some examples, processing circuitry of IMD 10 may determine an impedance value of patient 4 based on signals received from at least two of electrodes 16A-16D. For example, processing circuitry of IMD 10 may generate one of a current or voltage signal, deliver the signal via a selected two or more of electrodes 16A-16D, and measure the resulting other of current or voltage. Processing circuitry of IMD 10 may determine an impedance value based on the delivered current or voltage and the measured voltage or current.

In some examples, IMD 10 may include one or more additional sensors, such as one or more accelerometers (not shown) and/or one or more light sensors (not shown). Such accelerometers may be 3D accelerometers configured to generate signals indicative of one or more types of movement of the patient, such as gross body movement (e.g., motion) of the patient, patient posture, movements associated with the beating of the heart, or coughing, rales, or other respiration abnormalities. One or more of the parameters monitored by IMD 10 (e.g., impedance, EGM) may fluctuate in response to changes in one or more such types of movement. For example, changes in parameter values sometimes may be attributable to increased patient motion (e.g., exercise or other physical motion as compared to immobility) or to changes in patient posture, and not necessarily to changes in a medical condition. Thus, in some methods of determining an efficacy of a treatment program, it may be advantageous to account for such fluctuations when determining whether a change in a parameter is indicative of an improvement or a worsening of a medical condition of patient 4.

Figure 3:
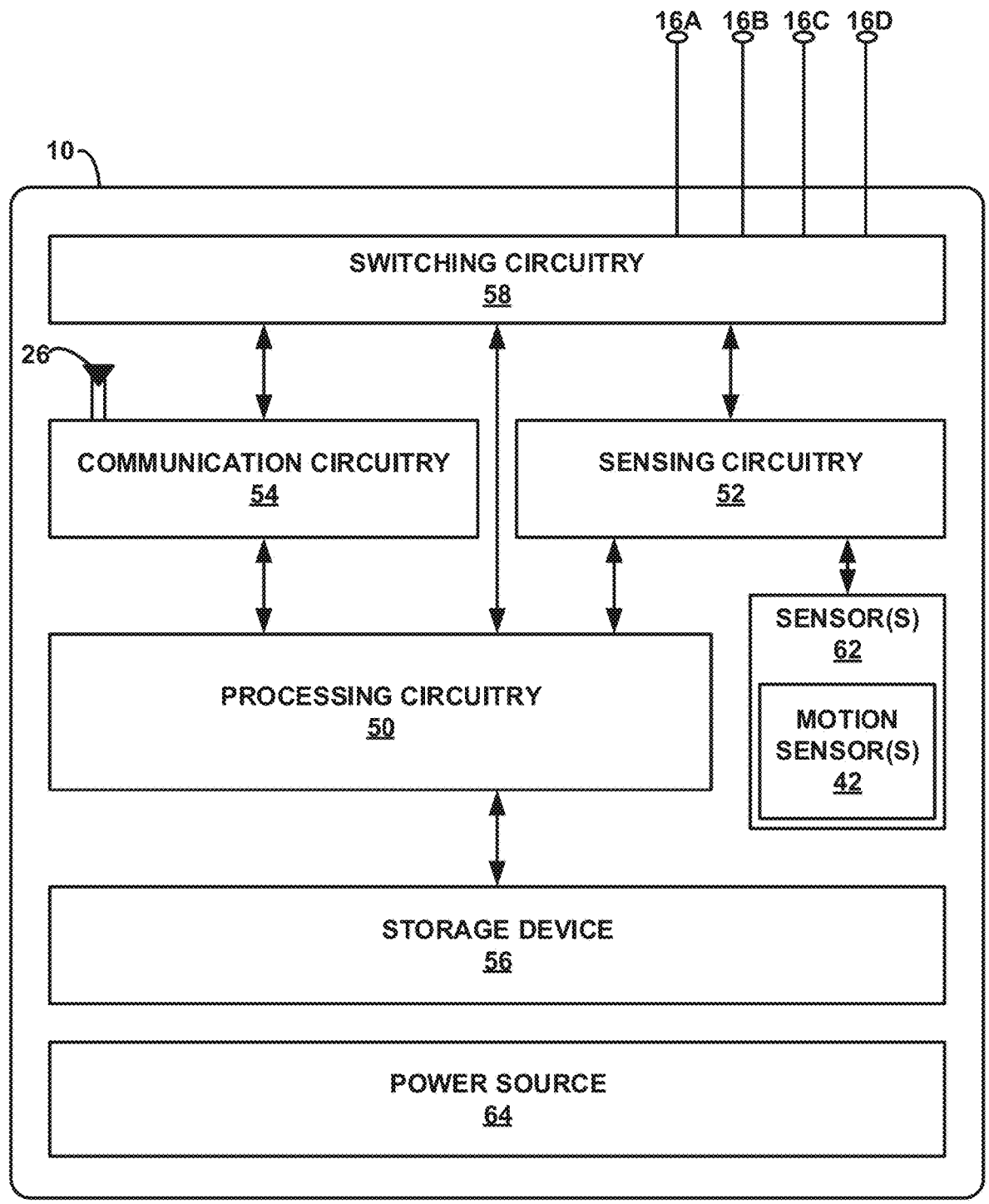
FIG. 3 is a functional block diagram illustrating an example configuration of the IMD of FIGS. 1 and 2, in accordance with one or more techniques described herein.

FIG. 3 is a functional block diagram illustrating an example configuration of IMD 10 of FIGS. 1 and 2, in accordance with one or more techniques described herein. In the illustrated example, IMD 10 includes electrodes 16, antenna 26, processing circuitry 50, sensing circuitry 52, communication circuitry 54, storage device 56, switching circuitry 58, sensors 62 including motion sensor(s) 42, and power source 64. Although not illustrated in FIG. 3, sensors 62 may include one or more light detectors.

Processing circuitry 50 may include fixed function circuitry and/or programmable processing circuitry. Processing circuitry 50 may include any one or more of a microprocessor, a controller, a DSP, an ASIC, an FPGA, or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Sensing circuitry 52 and communication circuitry 54 may be selectively coupled to electrodes 16A-16D via switching circuitry 58, as controlled by processing circuitry 50. Sensing circuitry 52 may monitor signals from electrodes 16A-16D in order to monitor electrical activity of heart (e.g., to produce an EGM), and/or subcutaneous tissue impedance, the impedance being indicative of at least some aspects of patient 4's respiratory patterns and the EMG being indicative of at least some aspects of patient 4's cardiac patterns. In some examples, a subcutaneous impedance signal collected by IMD 10 may indicate a respiratory rate and/or a respiratory intensity of patient 4 and an EMG collected by IMD 10 may indicate a heart rate of patient 4 and an atrial fibrillation (AF) burden of patient 4. Sensing circuitry 52 also may monitor signals from sensors 62, which may include motion sensor(s) 42, and any additional sensors, such as light detectors or pressure sensors, that may be positioned on IMD 10. In some examples, sensing circuitry 52 may include one or more filters and amplifiers for filtering and amplifying signals received from one or more of electrodes 16A-16D and/or motion sensor(s) 42.

Communication circuitry 54 may include any suitable hardware, firmware, software or any combination thereof for communicating with another device, such as external device 12 or another IMD or sensor, such as a pressure sensing device. Under the control of processing circuitry 50, communication circuitry 54 may receive downlink telemetry from, as well as send uplink telemetry to, external device 12 or another device with the aid of an internal or external antenna, e.g., antenna 26. In addition, processing circuitry 50 may communicate with a networked computing device via an external device (e.g., external device 12) and a computer network, such as the Medtronic CareLink® Network developed by Medtronic, plc, of Dublin, Ireland.

A clinician or other user may retrieve data from IMD 10 using external device 12, or by using another local or networked computing device configured to communicate with processing circuitry 50 via communication circuitry 54. The clinician may also program parameters of IMD 10 using external device 12 or another local or networked computing device.

In some examples, storage device 56 includes computer-readable instructions that, when executed by processing circuitry 50, cause IMD 10 and processing circuitry 50 to perform various functions attributed to IMD 10 and processing circuitry 50 herein. Storage device 56 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Power source 64 is configured to deliver operating power to the components of IMD 10. Power source 64 may include a battery and a power generation circuit to produce the operating power. In some examples, the battery is rechargeable to allow extended operation. In some examples, recharging is accomplished through proximal inductive interaction between an external charger and an inductive charging coil within external device 12. Power source 64 may include any one or more of a plurality of different battery types, such as nickel cadmium batteries and lithium ion batteries. A non-rechargeable battery may be selected to last for several years, while a rechargeable battery may be inductively charged from an external device, e.g., on a daily or weekly basis.

Figure 4A:
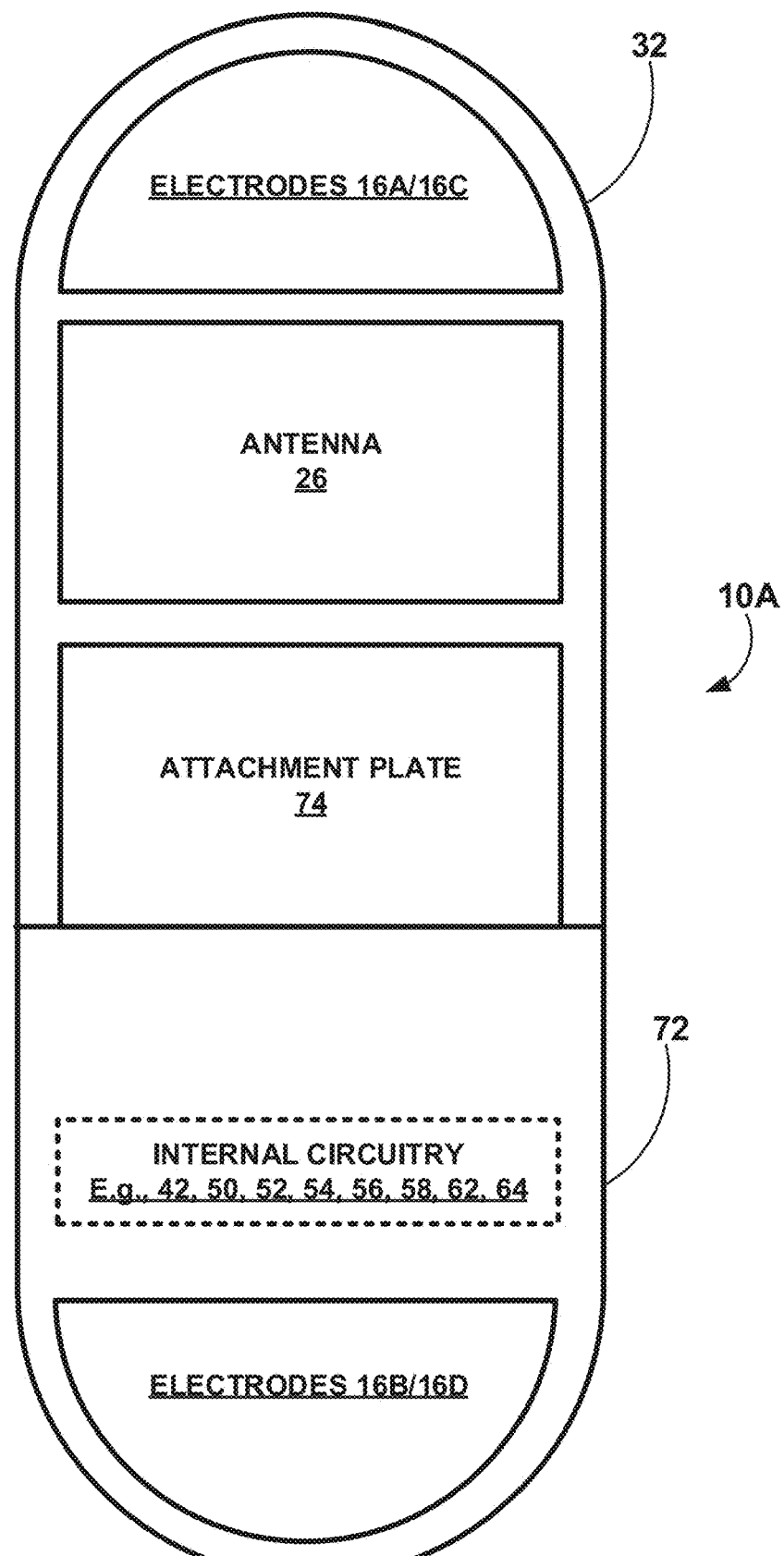
FIGS. 4A and 4B illustrate two additional example IMDs that may be substantially similar to the IMD of FIGS. 1-3, but which may include one or more additional features, in accordance with one or more techniques described herein.
Figure 4B:
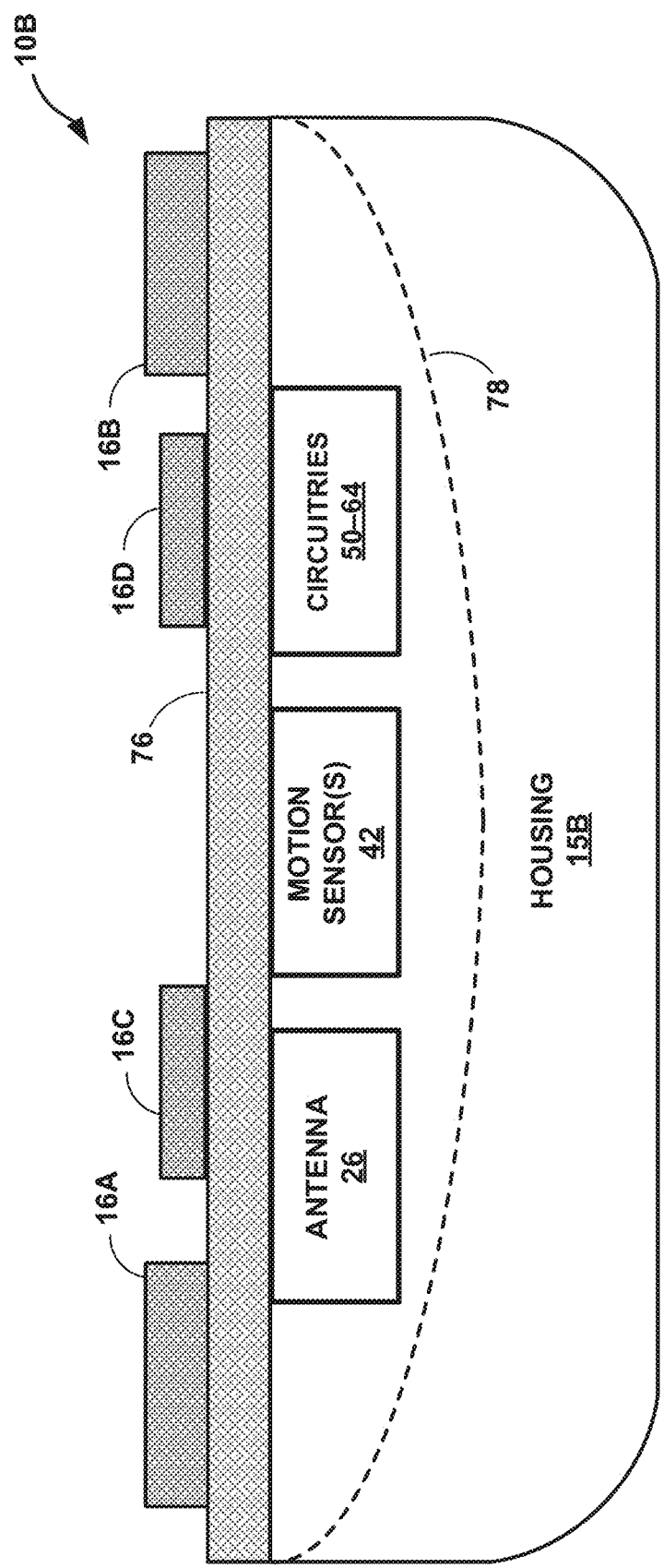

FIGS. 4A and 4B illustrate two additional example IMDs that may be substantially similar to IMD 10 of FIGS. 1-3, but which may include one or more additional features, in accordance with one or more techniques described herein. The components of FIGS. 4A and 4B may not necessarily be drawn to scale, but instead may be enlarged to show detail. FIG. 4A is a block diagram of a top view of an example configuration of an IMD 10A. FIG. 4B is a block diagram of a side view of example IMD 10B, which may include an insulative layer as described below.

FIG. 4A is a conceptual drawing illustrating another example IMD 10A that may be substantially similar to IMD 10 of FIG. 1. In addition to the components illustrated in FIGS. 1-3, the example of IMD 10 illustrated in FIG. 4A also may include a body portion 72 and an attachment plate 74. Attachment plate 74 may be configured to mechanically couple header assembly 32 to body portion 72 of IMD 10A. Body portion 72 of IMD 10A may be configured to house one or more of the internal components of IMD 10 illustrated in FIG. 3, such as one or more of processing circuitry 50, sensing circuitry 52, communication circuitry 54, storage device 56, switching circuitry 58, internal components of sensors 62, and power source 64. In some examples, body portion 72 may be formed of one or more of titanium, ceramic, or any other suitable biocompatible materials.

FIG. 4B is a conceptual drawing illustrating another example IMD 10B that may include components substantially similar to IMD 10 of FIG. 1. In addition to the components illustrated in FIGS. 1-3, the example of IMD 10B illustrated in FIG. 4B also may include a wafer-scale insulative cover 76, which may help insulate electrical signals passing between electrodes 16A-16D and processing circuitry 50. In some examples, insulative cover 76 may be positioned over an open housing 15B to form the housing for the components of IMD 10B. One or more components of IMD 10B (e.g., antenna 26, light emitter 38, processing circuitry 50, sensing circuitry 52, communication circuitry 54, switching circuitry 58, and/or power source 64) may be formed on a bottom side of insulative cover 76, such as by using flip-chip technology. Insulative cover 76 may be flipped onto a housing 15B. When flipped and placed onto housing 15B, the components of IMD 10B formed on the bottom side of insulative cover 76 may be positioned in a gap 78 defined by housing 15B.

Insulative cover 76 may be configured so as not to interfere with the operation of IMD 10B. For example, one or more of electrodes 16A-16D may be formed or placed above or on top of insulative cover 76, and electrically connected to switching circuitry 58 through one or more vias (not shown) formed through insulative cover 76. Insulative cover 76 may be formed of sapphire (i.e., corundum), glass, parylene, and/or any other suitable insulating material.

Figure 5:
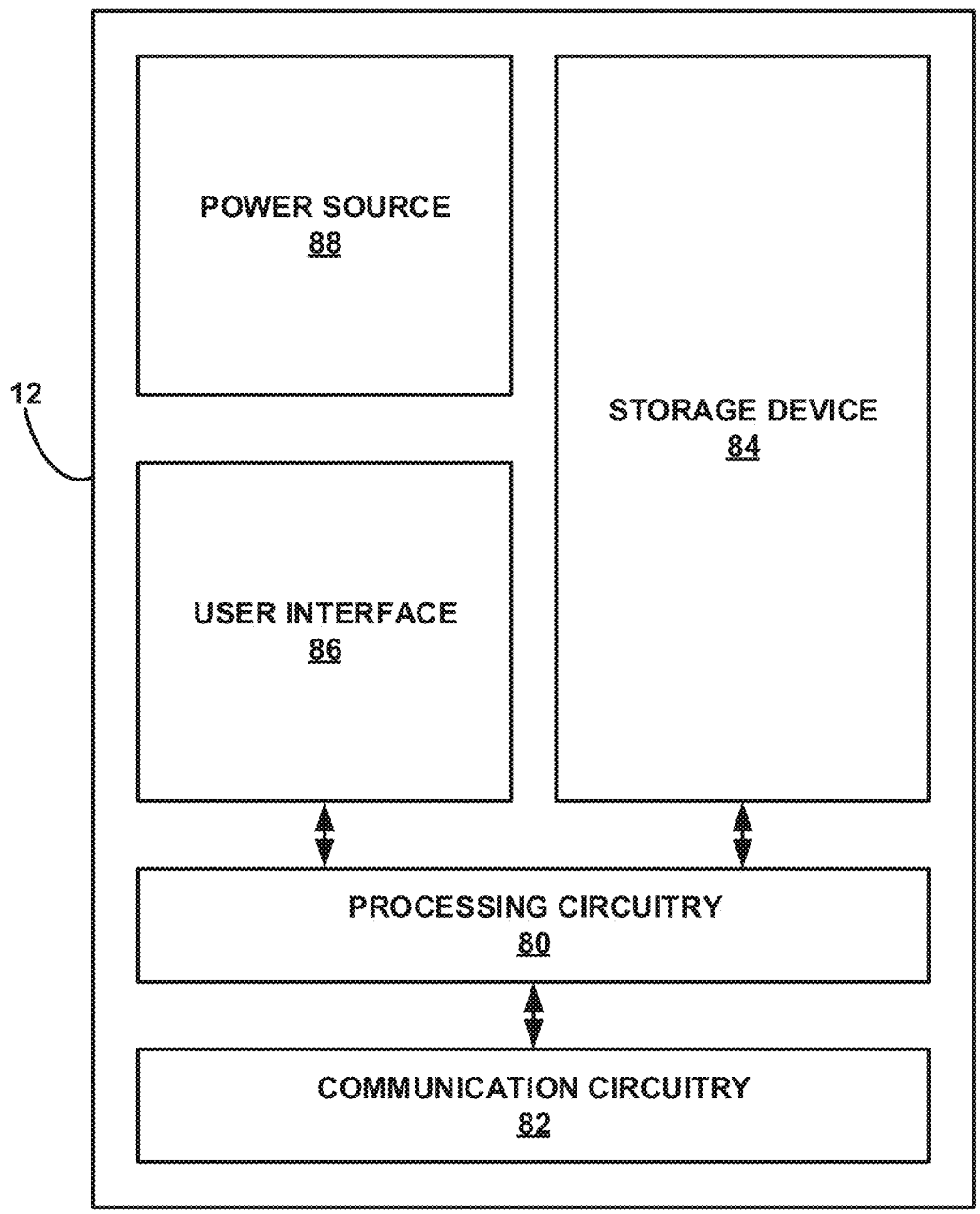
FIG. 5 is a block diagram illustrating an example configuration of components of the external device of FIG. 1, in accordance with one or more techniques of this disclosure.

FIG. 5 is a block diagram illustrating an example configuration of components of external device 12, in accordance with one or more techniques of this disclosure. In the example of FIG. 5, external device 12 includes processing circuitry 80, communication circuitry 82, storage device 84, user interface 86, and power source 88.

Processing circuitry 80, in one example, may include one or more processors that are configured to implement functionality and/or process instructions for execution within external device 12. For example, processing circuitry 80 may be capable of processing instructions stored in storage device 84. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

Communication circuitry 82 may include any suitable hardware, firmware, software or any combination thereof for communicating with another device, such as IMD 10. Under the control of processing circuitry 80, communication circuitry 82 may receive downlink telemetry from, as well as send uplink telemetry to, IMD 10, or another device.

Storage device 84 may be configured to store information within external device 12 during operation. Storage device 84 may include a computer-readable storage medium or computer-readable storage device. In some examples, storage device 84 includes one or more of a short-term memory or a long-term memory. Storage device 84 may include, for example, RAM, dynamic random access memories (DRAM), static random access memories (SRAM), magnetic discs, optical discs, flash memories, or forms of electrically programmable memories (EPROM) or EEPROM. In some examples, storage device 84 is used to store data indicative of instructions for execution by processing circuitry 80. Storage device 84 may be used by software or applications running on external device 12 to temporarily store information during program execution.

Data exchanged between external device 12 and IMD 10 may include operational parameters. External device 12 may transmit data including computer readable instructions which, when implemented by IMD 10, may control IMD 10 to change one or more operational parameters and/or export collected data. For example, processing circuitry 80 may transmit an instruction to IMD 10 which requests IMD 10 to export collected data (e.g., data corresponding to one or both of an ECG signal and an accelerometer signal) to external device 12. In turn, external device 12 may receive the collected data from IMD 10 and store the collected data in storage device 84. Additionally, or alternatively, processing circuitry 80 may export instructions to IMD 10 requesting IMD 10 to update electrode combinations for stimulation or sensing.

A user, such as a clinician or patient 4, may interact with external device 12 through user interface 86. User interface 86 includes a display (not shown), such as an LCD or LED display or other type of screen, with which processing circuitry 80 may present information related to IMD 10 (e.g., EGM signals obtained from at least one electrode or at least one electrode combination). In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 12 and provide input. In other examples, user interface 86 also includes audio circuitry for providing audible notifications, instructions or other sounds to patient 4, receiving voice commands from patient 4, or both. Storage device 84 may include instructions for operating user interface 86 and for managing power source 88.

Power source 88 is configured to deliver operating power to the components of external device 12. Power source 88 may include a battery and a power generation circuit to produce the operating power. In some examples, the battery is rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within external device 12. In other examples, traditional batteries (e.g., nickel cadmium or lithium ion batteries) may be used. In addition, external device 12 may be directly coupled to an alternating current outlet to operate.

Figure 6:
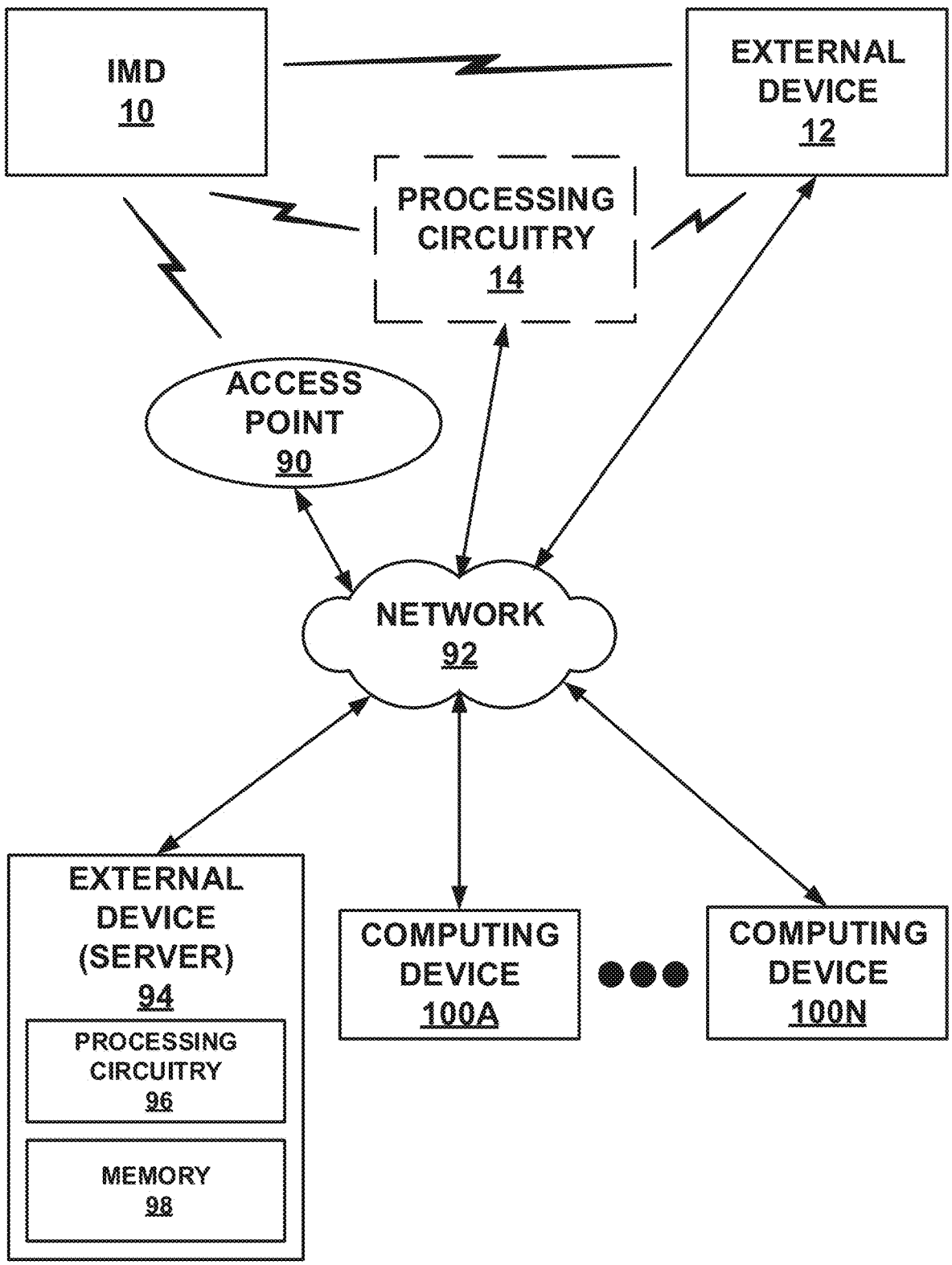
FIG. 6 is a block diagram illustrating an example system that includes an access point, a network, external computing devices, such as a server, and one or more other computing devices, which may be coupled to the IMD, the external device, and the processing circuitry of FIG. 1 via a network, in accordance with one or more techniques described herein.

FIG. 6 is a block diagram illustrating an example system that includes an access point 90, a network 92, external computing devices, such as a server 94, and one or more other computing devices 100A-100N, which may be coupled to IMD 10, external device 12, and processing circuitry 14 via network 92, in accordance with one or more techniques described herein. In this example, IMD 10 may use communication circuitry 54 to communicate with external device 12 via a first wireless connection, and to communication with an access point 90 via a second wireless connection. In the example of FIG. 6, access point 90, external device 12, server 94, and computing devices 100A-100N are interconnected and may communicate with each other through network 92.

Access point 90 may include a device that connects to network 92 via any of a variety of connections, such as telephone dial-up, digital subscriber line (DSL), or cable modem connections. In other examples, access point 90 may be coupled to network 92 through different forms of connections, including wired or wireless connections. In some examples, access point 90 may be a user device, such as a tablet or smartphone, that may be co-located with the patient. As discussed above, IMD 10 may be configured to transmit data, such as any one or combination of an EGM signal, an accelerometer signal, and a tissue impedance signal to external device 12. In addition, access point 90 may interrogate IMD 10, such as periodically or in response to a command from the patient or network 92, in order to retrieve parameter values determined by processing circuitry 50 of IMD 10, or other operational or patient data from IMD 10. Access point 90 may then communicate the retrieved data to server 94 via network 92.

In some cases, server 94 may be configured to provide a secure storage site for data that has been collected from IMD 10, and/or external device 12. In some cases, server 94 may assemble data in web pages or other documents for viewing by trained professionals, such as clinicians, via computing devices 100A-100N. One or more aspects of the illustrated system of FIG. 6 may be implemented with general network technology and functionality, which may be similar to that provided by the Medtronic CareLink® Network developed by Medtronic plc, of Dublin, Ireland.

Server 94 may include processing circuitry 96. Processing circuitry 96 may include fixed function circuitry and/or programmable processing circuitry. Processing circuitry 96 may include any one or more of a microprocessor, a controller, a DSP, an ASIC, an FPGA, or equivalent discrete or analog logic circuitry. In some examples, processing circuitry 96 may include multiple components, such as any combination of one or more microprocessors, one or more controllers, one or more DSPs, one or more ASICs, or one or more FPGAs, as well as other discrete or integrated logic circuitry. The functions attributed to processing circuitry 96 herein may be embodied as software, firmware, hardware or any combination thereof. In some examples, processing circuitry 96 may perform one or more techniques described herein based on an EGM signal, impedance signal, an accelerometer signal, or other sensor signals received from IMD 10, or parameter values determined based on such signals by IMD 10 and received from IMD 10, as examples. For example, processing circuitry may perform one or more of the techniques described herein to identify significant changes in one or more physiological parameters resulting from an event, such changes resulting from a medical treatment.

Server 94 may include memory 98. Memory 98 includes computer-readable instructions that, when executed by processing circuitry 96, cause IMD 10 and processing circuitry 96 to perform various functions attributed to IMD 10 and processing circuitry 96 herein. Memory 98 may include any volatile, non-volatile, magnetic, optical, or electrical media, such as RAM, ROM, NVRAM, EEPROM, flash memory, or any other digital media.

In some examples, one or more of computing devices 100A-100N (e.g., device 100A) may be a tablet or other smart device located with a clinician, by which the clinician may program, receive alerts from, and/or interrogate IMD 10. For example, the clinician may access data corresponding to any one or combination of an EGM signal, an accelerometer signal, an impedance signal, and other types of signals collected by IMD 10, or parameter values determined by IMD 10 based on such signals, through device 100A, such as when patient 4 is in between clinician visits, to check on a status of a medical condition. In some examples, the clinician may enter instructions for a medical intervention for patient 4 into an app in device 100A, such as based on a status of a patient condition determined by IMD 10, external device 12, processing circuitry 14, or any combination thereof, or based on other patient data known to the clinician. Device 100A then may transmit the instructions for medical intervention to another of computing devices 100A-100N (e.g., device 100B) located with patient 4 or a caregiver of patient 4. For example, such instructions for medical intervention may include an instruction to change a drug dosage, timing, or selection, to schedule a visit with the clinician, or to seek medical attention. In further examples, device 100B may generate an alert to patient 4 based on a status of a medical condition of patient 4 determined by IMD 10, which may enable patient 4 proactively to seek medical attention prior to receiving instructions for a medical intervention. In this manner, patient 4 may be empowered to take action, as needed, to address his or her medical status, which may help improve clinical outcomes for patient 4.

Figure 7:
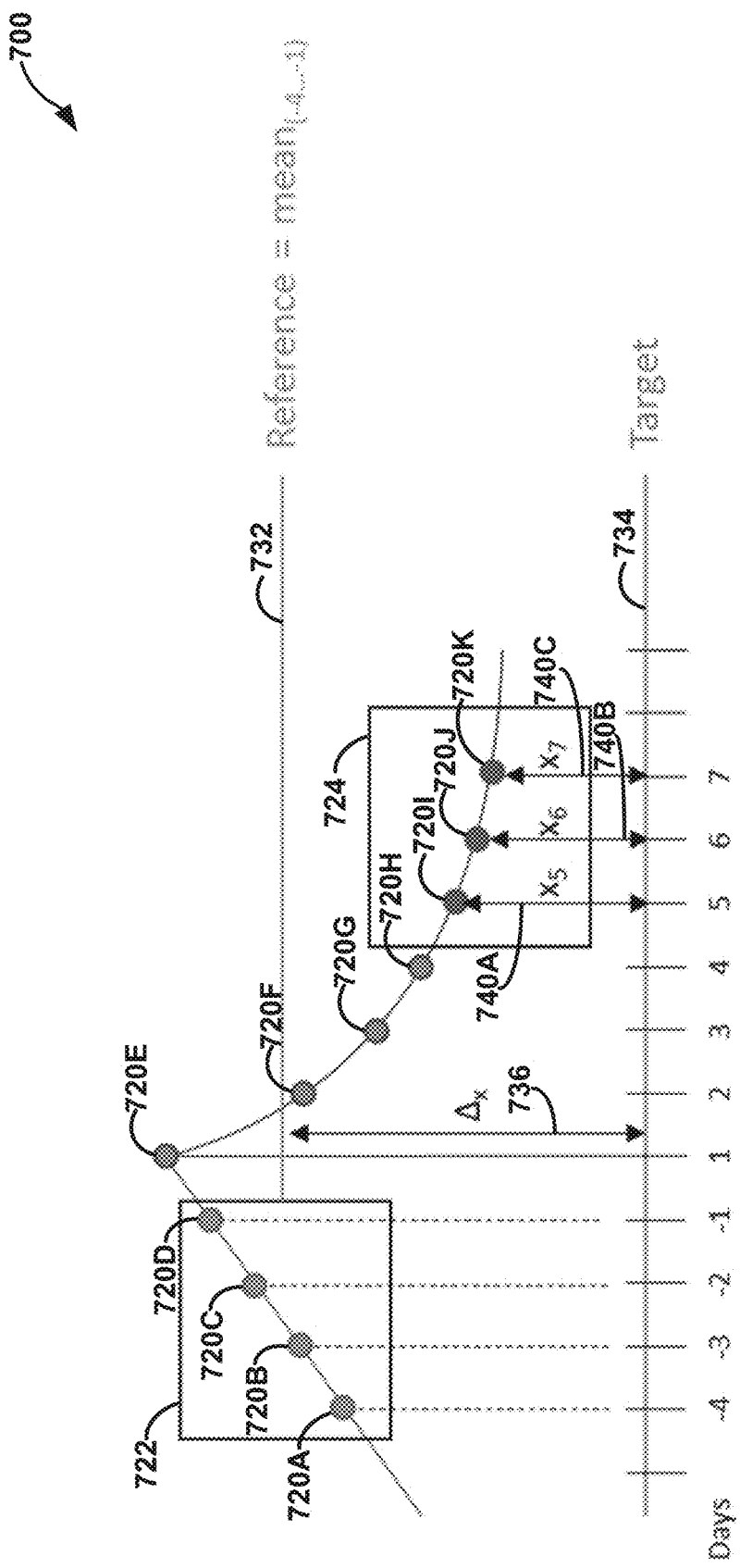
FIG. 7 is a graph illustrating a sequence of parameter values and a set of first difference values, in accordance with one or more techniques described herein.

FIG. 7 is a graph 700 illustrating a sequence of parameter values 720A-720K and a set of first difference values 740A-740C, in accordance with one or more techniques described herein. The sequence of parameter values 720A-720K (collectively, "parameter values 720") includes a first group of parameter values 722 and a second group of parameter values 724. Additionally, graph 700 illustrates reference parameter value 732, target parameter value 734, delta value 736, and first difference values 740A-740C (collectively, "first difference values 740").

In some examples, IMD 10 may collect the sequence of parameter values 720 at a predetermined frequency. For example, IMD 10 may collect one parameter value of the sequence of parameter values 720 per day (e.g., a time interval of 24 hours may separate a parameter value of the sequence of parameter values 720 and each respective consecutive parameter value of the sequence of parameter values 720). In other words, 24 hours may elapse between a time in which IMD 10 measures, parameter value 720A and a time in which IMD 10 measures parameter value 720B, 24 hours may elapse between a time in which IMD 10 measures parameter value 720B and a time in which IMD 10 measures parameter value 720C, 24 hours may elapse between a time in which IMD 10 measures parameter value 720C and a time in which IMD 10 measures parameter value 720D, and so on. However, it is not required that IMD 10 collects parameter values 720 at a frequency of one parameter value per day. IMD 10 may collect parameter values 720 at any frequency (e.g., one parameter value per hour, one parameter value every other day, or one parameter value per minute). Additionally, in some examples, the measured value of the parameter for a period, such as a day, may represent a plurality of values determined during the period, such as being a mean, median, or other statistical representation of values determined the period. As one example, each parameter value of a sequence of parameter values may represent a daily average value of the parameter. In other examples, each parameter value of a sequence of parameter values may represent a first parameter value measured in a given time period or a last parameter value measured in a given time period. In some examples, the resolution of periodic measurements may change automatically or change manually from daily to hourly or every minute depending on the data measured prior or the interventions that the patient receives.

Processing circuitry 14 may determine whether the sequence of parameter values 720 indicate an improvement or a worsening of patient 4 responsive to a treatment program delivered to patient 4 during a period of time in which IMD 10 collects the sequence of parameter values 720. In some examples, the treatment program begins at a time that is closer to a time in which IMD 10 collects parameter value 720E than respective times in which IMD 10 collects any other parameter value of the sequence of parameter values 720E. For example, the treatment program may begin on a same day in which IMD 10 collects parameter value 720E. Processing circuitry 14, in some cases, may receive data indicating a time in which the treatment program begins. Subsequently, processing circuitry 14 may determine that parameter value 720E of the sequence of parameter values 720 represents the parameter value which is closest to the time in which the treatment program begins.

To determine whether patient 4 is experiencing an improvement or a worsening from one or more conditions and/or symptoms responsive to receiving a treatment program, processing circuitry 14 may determine whether the sequence of parameter values 720 significantly change from a period of time before the treatment program begins to a period of time after the treatment program begins and/or a period of time after the treatment program concludes. Processing circuitry 14 may select the first set of parameter values 722 and select the second set of parameter values 724. As seen in FIG. 7, processing circuitry 14 may select the first set of parameter values 722 to include parameter value 720A, parameter value 720B, parameter value 720C, and parameter value 720D, each of these parameter values being collected by IMD 10 before parameter value 720E which corresponds to the start of the treatment program. Additionally, processing circuitry 14 may select the second set of parameter values 724 to include parameter value 720I, parameter value 720J, and parameter value 720K, each of these parameter values being collected by IMD 10 after parameter value 720E which corresponds to the start of the treatment program. In this way, processing circuitry 14 may determine if a clinically significant change is detectable from the first set of parameter values 722 to second set of parameter values 722, the clinically significant change indicating whether patient 4 is experiencing an improvement or a worsening.

Processing circuitry 14 may, for example, determine reference parameter value 732 based on the sequence of parameter values 720. In some cases, processing circuitry 14 may calculate reference parameter value 732 to be a mean of the first set of parameter values 722. In some cases, processing circuitry 14 may calculate reference parameter value 732 to be a median of the first set of parameter values 722. In some cases, processing circuitry 14 may calculate reference parameter value 732 to be any statistical representation of the first set of parameter values 722. In this way, reference parameter value 732 may represent a baseline of the respective parameter that is tracked by the sequence of parameter values 720 while patient 4 is experiencing one or more conditions and before patient 4 receives treatment. In some cases, processing circuitry 14 may receive information including a user selection reference parameter value 732. In some examples, processing circuitry 14 receives information indicative of a time corresponding to an event, such as the start time of the treatment program. In turn, processing circuitry 14 may select a parameter value closest in time to the reference time to be the reference parameter value. In some examples, processing circuitry 14 may output the sequence of parameter values 720 for display by a user interface, and in turn, processing circuitry 14 may receive the information including the user selection reference parameter value 732.

In some examples, to determine whether patient 4 is experiencing an improvement or a worsening of a medical condition, processing circuitry 14 may identify a target parameter value 734 and determine whether the sequence of parameter values 720 significantly trend closer to the target parameter value 734 during a period of time following the start of a treatment program administered to patient 4 as compared with a period of time before the start of the treatment program. Processing circuitry 14 may, in some cases, determine target parameter value 734 based on reference parameter value 732. For example, processing circuitry 14 may calculate target parameter value 734 by subtracting delta value 736 from reference parameter value 732. In some examples, processing circuitry 14 may calculate target parameter value 734 by determining a product of reference parameter value 732 and a predetermined fraction, and subsequently determine delta value 736 by subtracting target parameter value 734 from reference parameter value 732. In some examples, processing circuitry 14 receives information including the target parameter value 734. For example, processing circuitry 14 may output the sequence of parameter values 720 for display by a user interface, and in turn, processing circuitry 14 may receive the information including the user selection of the target parameter value 734.

In one or more examples where processing circuitry 14 calculates target parameter value 734 by subtracting delta value 736 from reference parameter value 732, delta value 736 may represent a different predetermined value corresponding for each parameter. For example, when parameter values 720 represent subcutaneous impedance values, delta value 736 may be within a range from 50 ohms (Ω) to 300Ω (e.g., 250Ω), when parameter values 720 represent respiratory rate values, delta value 736 may be within a range from 1 breaths per minute to 5 breaths per minute (e.g., three breaths per minute), when parameter values 720 represent night time heart rate values, delta value 736 may be within a range from 1 beats per minute to 7 beats per minute (e.g., 5 beats per minute), when parameter values 720 represent ventricular rate values during atrial fibrillation, delta value 736 may be within a range from 20 beats per minute to 80 beats per minute (e.g., 60 beats per minute), and when parameter values 720 represent atrial fibrillation burden, delta value 736 may be within a range from 0.5 hours to 3 hours (e.g., 2 hours).

Processing circuitry 14 may determine whether patient 4 experiences an improvement or a worsening of a medical condition or a physiological parameter based on the sequence of parameter values 720 (e.g., the first set of parameter values 722 and the second set of parameter values 724), the reference parameter value 732, and the target parameter value 734. In some examples, processing circuitry 14 selects the second set of parameter values 724 based on the time in which the treatment program begins. For example, processing circuitry 14 may select the second set of parameter values 724 to include parameter value 720I which is collected by IMD 10 four days after parameter value 720E, parameter value 720J which is collected by IMD 10 five days after parameter value 720E, and parameter value 720K which is collected by IMD 10 six days after parameter value 720E. As such, three parameter values (i.e., parameter value 720F, parameter value 720G, and parameter value 720H) separate parameter value 720E, which corresponds to the start of the treatment program, and the second set of parameter values 724. It may be beneficial for processing circuitry 14 to select parameter value 720I, parameter value 720J, and parameter value 720K as the second set of parameter values 724 so that a gap of time exists between the start of the treatment program and the second set of parameter values 724 used by processing circuitry 14 to determine whether the treatment program causes an improvement or a worsening in a medical condition or a physiological parameter of patient 4.

In some examples, processing circuitry 14 may calculate a parameter change value based on the first set of parameter values 732 and the second set of parameter values 734. Additionally, processing circuitry 14 may determine whether the parameter change value indicates one or more conditions and/or one or more symptoms of patient 4 have improved or worsened. In some cases, processing circuitry 14 may calculate the parameter change value using equation 1.

$$\text{parameter change value} = \frac{\sum \text{reference} - \text{difference}_i}{\text{reference} - \text{target}} = \frac{(\Delta_x - x_5) + (\Delta_x - x_6) + (\Delta_x - x_7)}{\Delta_x} \quad (\text{eq. 1})$$

In the example of FIG. 7, the value $\Delta_x$ represents delta value 736, the value $x_5$ represents difference value 740A, the value $x_6$ represents difference value 740B, and the value $x_7$ represents difference value 740C.

In some examples, processing circuitry 14 may determine whether the set of parameter values 720 values indicate an improvement or a worsening of patient 4 by comparing the parameter change value to a threshold parameter change value. Processing circuitry 14 may determine that the set of parameter values 720 indicate an improvement or a worsening of patient 4 if the parameter change value is greater than the threshold parameter change value and processing circuitry 14 may determine that the set of parameter values 720 do not indicate an improvement or a worsening of patient 4 if the parameter change value is not greater than the threshold parameter change value. In some examples, the threshold parameter change value is within a range from 0.5 to 0.9 (e.g., 0.7), but this is not required. The threshold parameter change value may include any value or range of values.

In some examples, processing circuitry 14 may determine whether an improvement or a worsening has occurred in patient 4 by determining whether more than one set of parameter values corresponding to more than one parameter indicate an improvement or a worsening of a medical condition or a physiological parameter patient 4. For example, IMD 10 may collect a set of parameter values corresponding to each of a subcutaneous impedance of patient 4, a respiratory rate of patient 4, a heart rate of patient 4, an AF burden of patient 4, a ventricular rate of patient 4 while patient 4 is experiencing AF, or any combination thereof. Processing circuitry 14 may calculate a parameter change value corresponding to each parameter of the set of parameters and compare each respective parameter change value to a threshold parameter change value. Based on a number of parameter change values corresponding to a parameter that are greater than the threshold parameter change value, processing circuitry 14 may determine whether an improvement or a worsening of a medical condition has occurred in patient 4.

In some examples, the first set of parameter values 722 and the second set of parameter values 724 are fixed at 4 parameter values and 3 parameter values, respectively, but this is not required. The first set of parameter values 722 and the second set of parameter values 724 may include any number of parameter values. In some examples, the last parameter value of the first set of parameter values 722 is fixed as the last parameter value collected by IMD 10 before the parameter value corresponding to the start of the treatment program (e.g., parameter value 720E), but this is not required. The last parameter value of the first set of parameter values 722 may be any parameter value collected by IMD 10 before the parameter value corresponding to the start of the treatment program. In some examples, processing circuitry 14 may select the first set of parameter values 722 backwards from the last parameter value of the first set of parameter values 722. Processing circuitry 14 may select the second set of parameter values 724 to include any set of parameter values 720 collected by IMD 10 following the start of the treatment program. In examples where the second set of parameter values 724 includes three parameter values, processing circuitry 14 may select the last parameter value of the second set of parameter values 724 to be at most three parameters following the parameter value corresponding to the start of the treatment program. In the example of FIG. 7, processing circuitry 14 selects the last parameter value of the second set of parameter values 724 to be six parameter values following the parameter value corresponding to the start of the treatment program.

Figure 8:
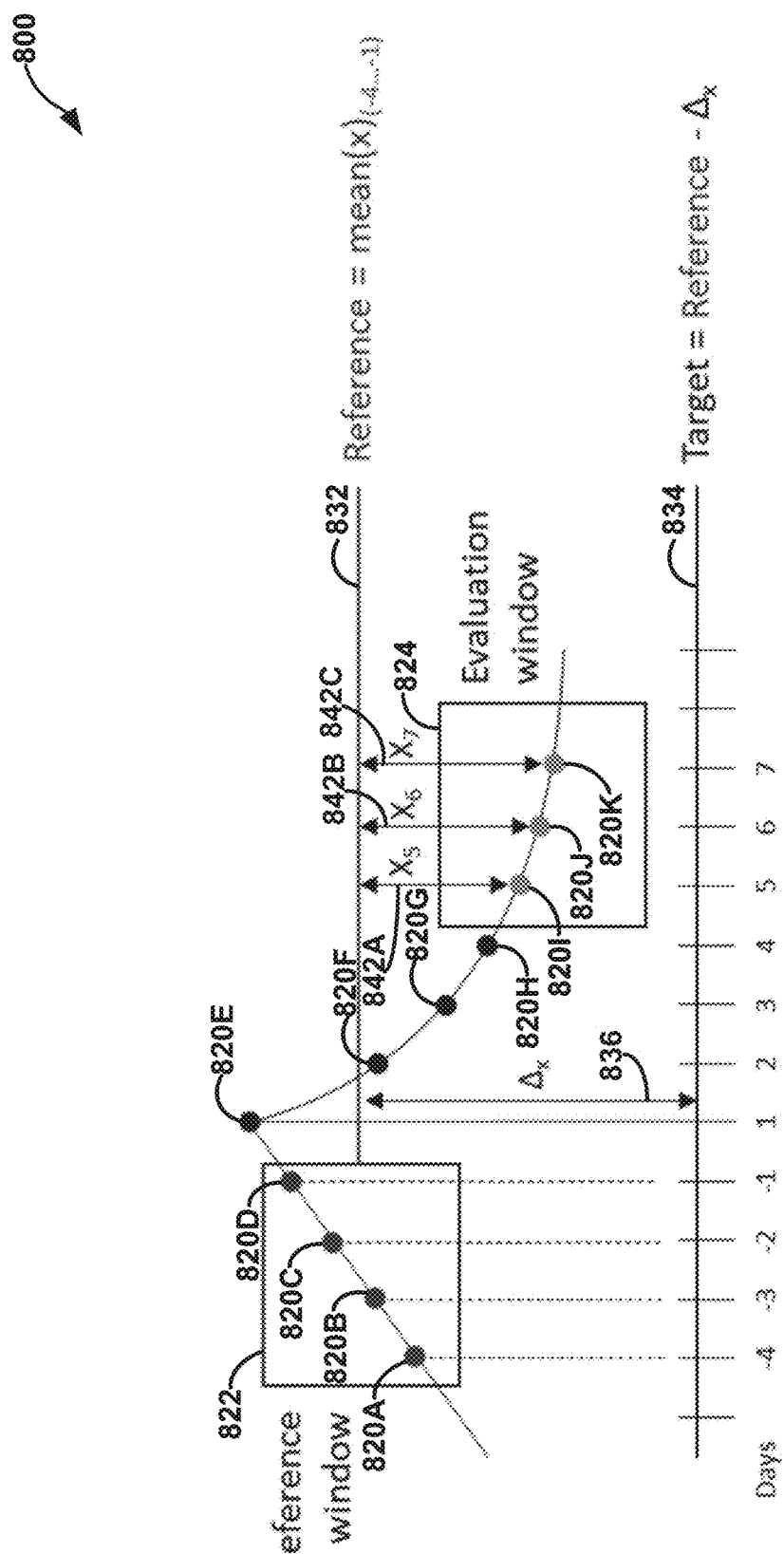
FIG. 8 is a graph illustrating a sequence of parameter values and a set of second difference values, in accordance with one or more techniques described herein.

FIG. 8 is a graph 800 illustrating a sequence of parameter values 820A-820K and a set of second difference values 842A-842C, in accordance with one or more techniques described herein. The sequence of parameter values 820A-820K (collectively, "parameter values 820") includes a first group of parameter values 822 and a second group of parameter values 824. Additionally, graph 800 illustrates reference parameter value 832, target parameter value 834, delta value 836, and second difference values 842A-842C (collectively, "difference values 842"). FIG. 8 may be substantially the same as FIG. 7 except that the set of second difference values 842 represent differences between reference parameter value 832 and respective parameter values of the second group of parameter values 824, whereas the set of first difference values 740 of FIG. 7 represent differences between target parameter value 734 and respective parameter values the second group of parameter values 724.

In some examples, processing circuitry 14 may calculate a parameter change value based on the first set of parameter values 832 and the second set of parameter values 834. Additionally, processing circuitry 14 may determine whether the parameter change value indicates whether one or more conditions and/or one or more symptoms of patient 4 have improved or worsened. In some cases, processing circuitry 14 may calculate the parameter change value using equation 2.

$$\text{parameter change value} = \frac{X_5 + X_6 + X_7}{\Delta_x} \quad (\text{eq. 2})$$

In the example of FIG. 8, the value $\Delta_x$ represents delta value 836, the value $X_5$ represents difference value 842A, the value $X_6$ represents difference value 842B, and the value $X_7$ represents difference value 842C.

Figure 9:
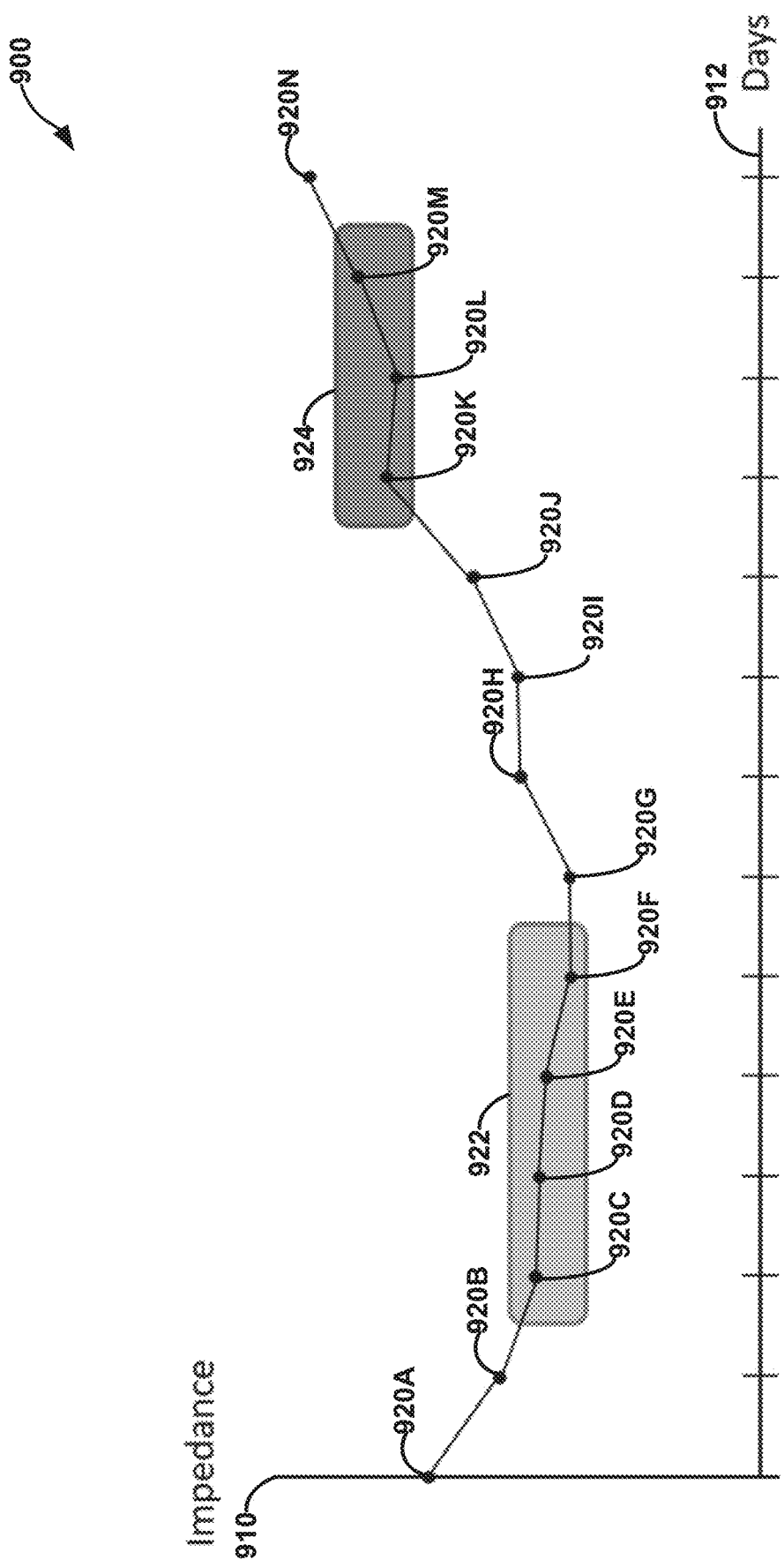
FIG. 9 is a graph illustrating a sequence of impedance parameter values which are measured by the IMD of FIG. 1 over a period of time, in accordance with one or more techniques described herein.

FIG. 9 is a graph 900 illustrating a sequence of impedance parameter values 920A-920N which are measured by IMD 10 over a period of time, in accordance with one or more techniques described herein. The sequence of impedance parameter values 920A-920N (collectively, "impedance parameter values 920") includes a first group of parameter values 922 and a second group of parameter values 924.

Each impedance parameter value of impedance parameter values 920 may be recorded by IMD 10 on a respective day of days 912. For example, IMD 10 may record impedance parameter value 920A on a first day, record impedance parameter value 920B on a second day, recording impedance parameter value 920C on a third day, and so on. In some examples, each impedance parameter value of impedance parameter values 920 may be recorded at the same time each day. That is, any given impedance parameter values 920 may be recorded 24 hours apart from consecutive impedance parameter values of impedance parameter values 920. In some examples, impedance parameter values 920 may be recorded by IMD 10 according to an interval other than once per day (e.g., once per hour, twice per hour, twice per day, once every two days, or any other interval).

In some examples, a trigger event may occur near a time in which IMD 10 collects impedance parameter value 920G. Processing circuitry 14 may determine that impedance parameter value 920G is closer to the trigger event than any other impedance parameter value of impedance parameter values 920. Processing circuitry 14 may receive a timestamp which indicates a time in which the trigger event occurs. For example, the trigger event may represent a user indication of a time of a start of a treatment program or a time of a change in a treatment program. Additionally, or alternatively, the trigger event may represent a time in which processing circuitry 14 determines that patient 4 is at high risk of experiencing a condition (e.g., a high risk of experiencing heart failure). For example, IMD 110 may calculate a heart failure risk score corresponding to patient 4. If the heart failure risk score increases above a threshold heart failure risk score, processing circuitry 14 may trigger a trigger event and select impedance parameter value 920G as being the closest parameter value to a time in which the heart failure risk score increases above a threshold heart failure risk score.

In some examples, processing circuitry 14 may select the first group of parameter values 922 and the second group of parameter values 924 from impedance parameter values 920 responsive to determining that impedance parameter value 920G corresponds to the trigger event. For example, processing circuitry 14 may select the first group of parameter values 922 to include the four impedance parameter values preceding impedance parameter value 920G (e.g., impedance parameter values 920C-920F), which corresponds to the trigger event. In this way, the first group of parameter values 922 may represent "reference" parameter values which indicate a baseline impedance before the reference event occurs. Processing circuitry 14 may select the second group of parameter values 924 to include the three consecutive impedance parameter values that end with the impedance parameter value collected by IMD 10 seven parameter values after the end of the first group of parameter values 922. In other words, processing circuitry 14 may select the second group of parameter values 924 to include impedance parameter values 920K-920M. The second group of parameter values 924 may represent "evaluation" parameter values which processing circuitry 14 may compare with the reference parameter values of the first group of parameter values 922.

In some examples, processing circuitry 14 selects the first group of parameter values 922 and the second group of parameter values 924 based on a current day in which impedance parameter values 920 are analyzed. For example, when a current day represents the day in which IMD 10 measures impedance parameter value 920M. Processing circuitry 14 may select the second group of parameter values 924 to include a group of consecutive parameter values that ends with the impedance parameter value collected by IMD 10 collected on the current day. In the example of graph 900, processing circuitry 14 selects the second group of parameter values 924 to include impedance parameter values 920K-920M, where impedance parameter value 920M is collected by IMD 10 on the current day. Processing circuitry 14 may select the first group of parameter values 922 to include a set of consecutive parameter values ending a number of days (e.g., 7 days) before the current day. In the example of graph 900, processing circuitry 14 may select the first group of parameter values 922 to include impedance parameter values 920C-920F, where impedance parameter value 920F is collected by IMD 10 seven days prior to the current day.

Selection of the first group of parameter values 922 and the second group of parameter values 924 based on the current day may allow processing circuitry 14 to determine whether a change in impedance occurs from a baseline impedance a week before the current day to an impedance immediately preceding the current day. In this way, the first group of parameter values 922 and the second group of parameter values 924 may represent rolling windows of parameter values which change based on the current day. For example, when the current day advances from the day in which IMD 10 collects impedance parameter value 920M to the day in which IMD 10 collects impedance parameter value 920N, processing circuitry 14 may update the first group of parameter values 922 to include impedance parameter values 920D-920G and processing circuitry 14 may update the second group of parameter values 924 to include impedance parameter values 920L-920N.

In the case of impedance, an increase in impedance parameter values responsive to a trigger event may represent a significant improvement in a patient condition. For parameters other than impedance (e.g., respiratory rate, night heart rate, and AF burden), a decrease in parameter values responsive to a trigger event may represent a significant improvement in a patient condition.

Figure 10:
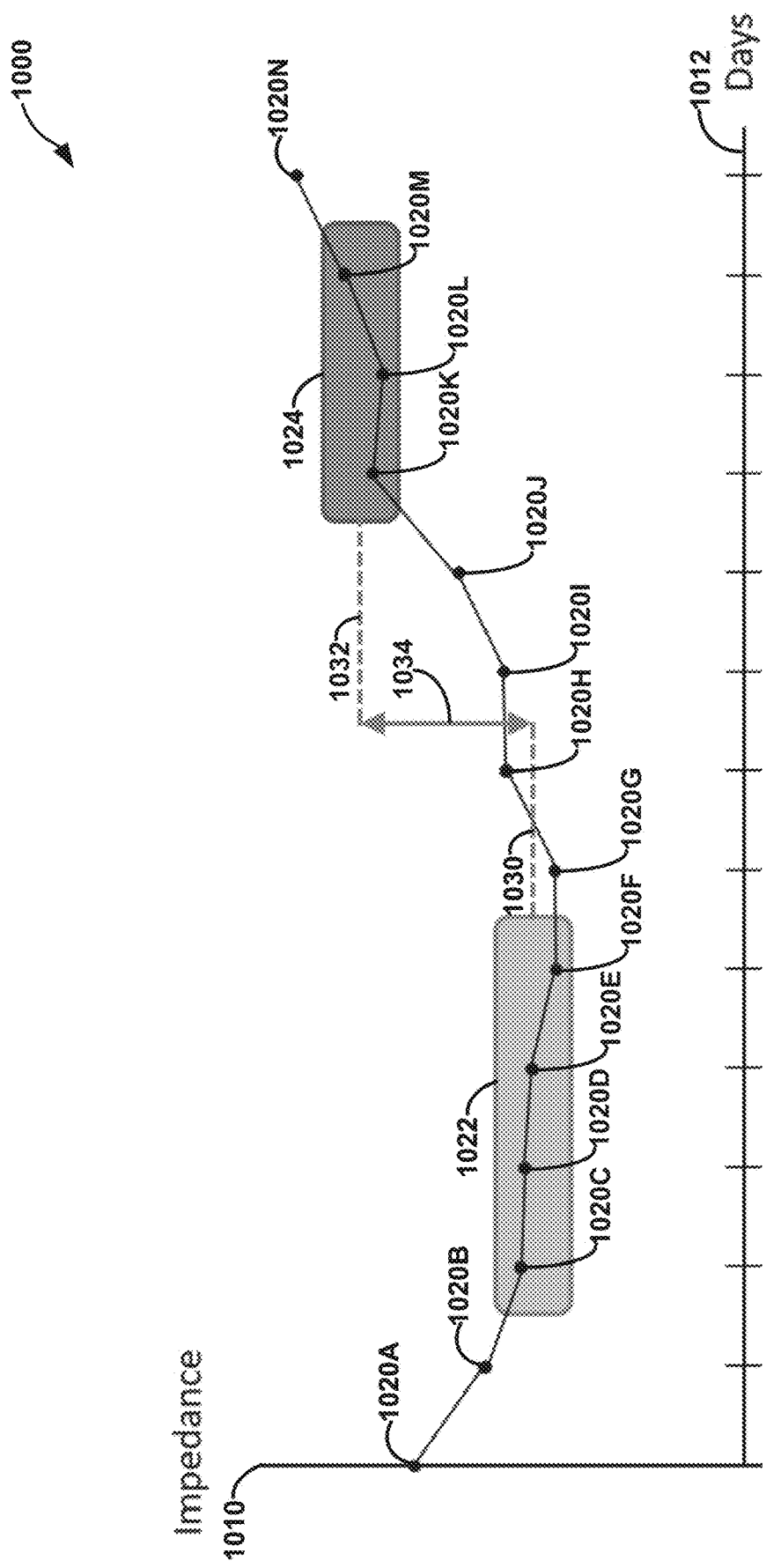
FIG. 10 is a graph illustrating a sequence of impedance parameter values, a mean baseline impedance, and a mean evaluation impedance, in accordance with one or more techniques described herein.

FIG. 10 is a graph 1000 illustrating a sequence of impedance parameter values 1020A-1020N, a baseline impedance 1030, and an evaluation impedance 1032, in accordance with one or more techniques described herein. The sequence of impedance parameter values 1020A-1020N (collectively, "impedance parameter values 1020") includes a first group of parameter values 1022 and a second group of parameter values 1024. Graph 1000 of FIG. 10 may be substantially the same as graph 900 of FIG. 9 except that graph 1000 includes the baseline impedance 1030, the evaluation impedance 1032, and an impedance difference 1034.

In some examples, processing circuitry 14 may calculate the baseline impedance 1030 by calculating a mean of the first group of parameter values 1022, determining a median of the first group of parameter values 1022, or determining another statistical representation of the first group of parameter values 1022. Processing circuitry 14 may calculate the evaluation impedance 1032 by calculating a mean of the second group of parameter values 1024, determining a median of the second group of parameter values 1024, or determining another statistical representation of the second group of parameter values 1024. Subsequently, processing circuitry 14 may calculate the difference 1034 between the baseline impedance 1030 and the evaluation impedance 1032. If the difference 1034 is greater than a threshold impedance difference value, processing circuitry 14 may determine whether a patient condition is improved. In one example, the threshold impedance difference value is 50 Ohms (Ω), meaning that the evaluation impedance 1032 must be more than 50Ω higher than the baseline impedance 1030 for processing circuitry 14 to determine that a patient condition is improved.

Figure 11:
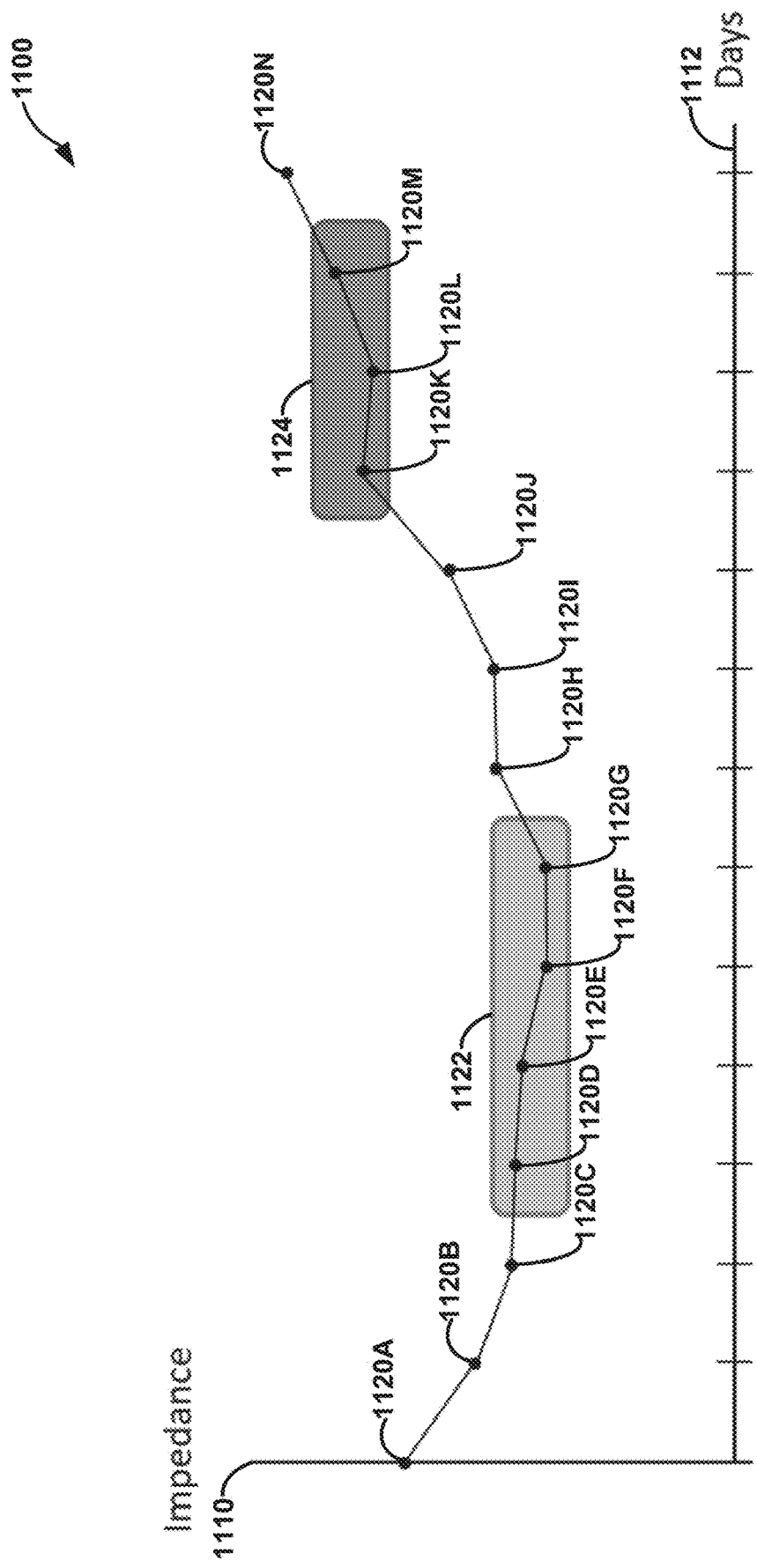
FIG. 11 is a graph illustrating a sequence of impedance parameter values, in accordance with one or more techniques described herein.

FIG. 11 is a graph 1100 illustrating a sequence of impedance parameter values 1120A-1120N, in accordance with one or more techniques described herein. The sequence of impedance parameter values 1120A-1120N (collectively, "impedance parameter values 1120") includes a first group of parameter values 1122 and a second group of parameter values 1124.

Each impedance parameter value of impedance parameter values 1120 may be recorded by IMD 10 on a respective day of days 1112. For example, IMD 10 may record impedance parameter value 1120A on a first day, record impedance parameter value 1120B on a second day, recording impedance parameter value 1120C on a third day, and so on. In some examples, each impedance parameter value of impedance parameter values 1120 may be recorded at the same time each day. That is, any given impedance parameter value of impedance parameter values 1120 may be recorded 24 hours apart from consecutive impedance parameter values of impedance parameter values 1120. In some examples, impedance parameter values 1120 may be recorded by IMD 10 according to an interval other than once per day (e.g., once per hour, twice per hour, twice per day, once every two days, or any other interval).

Graph 1100 may be substantially the same as graph 900 of FIG. 9, except that the first group of parameter values 1122 is closer to the second group of parameter values 1124. In some examples, processing circuitry 14 may select the first group of parameter values 1122 and the second group of parameter values 1124 based on user input. For example, processing circuitry 14 may receive user input which indicates that an intervention begins on a day in which IMD 10 collects impedance parameter value 1120H. Subsequently, processing circuitry 14 may select the first group of parameter values 1122 and the second group of parameter values 1124 based on the selected start date.

Figure 12:
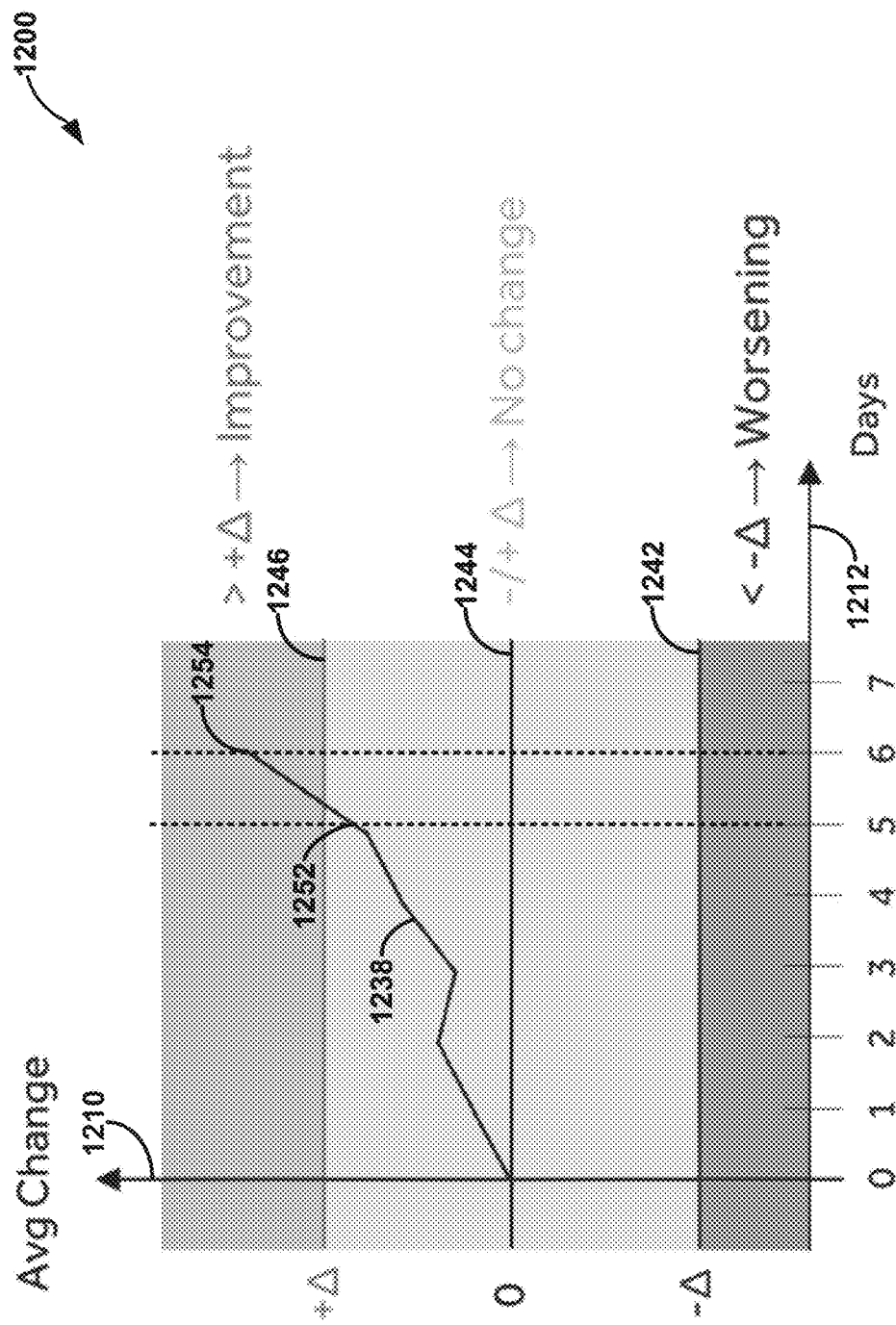
FIG. 12 is a graph illustrating a parameter plot in relation to a worsening threshold and an improvement threshold, in accordance with one or more techniques described herein.

FIG. 12 is a graph 1100 illustrating a parameter plot 1238 in relation to a worsening threshold 1242 and an improvement threshold 1246, in accordance with one or more techniques described herein. Parameter plot 1238 represents a parameter 1210 measured by IMD 110 over a number of days 1212. As seen in FIG. 12, the parameter plot 1238 increases from day 0 to day 6.

The worsening threshold 1242 represents a threshold by which processing circuitry 14 determines if the parameter 1210 indicates that a patient conditioning is worsening. For example, baseline parameter value 1244 may represent a baseline value of parameter 1210. In some examples, baseline parameter value 1244 may represent a mean of a group of parameter values preceding a trigger event. In some examples, baseline parameter value 1244 may represent a value of parameter 1210 at a trigger event. Processing circuitry 14 may determine that a parameter indicates a worsening of a patient condition if the parameter decreases below the worsening threshold 1242. Alternatively, processing circuitry 14 may determine that a parameter indicates an improvement of a patient condition if the parameter increases above the improvement threshold 1246. For example, as seen in graph 1200, parameter plot 1238 is at value 1252 on day 5 and parameter plot 1238 is at value 1254 in day 6. Value 1252 is lower than the improvement threshold 1246 and value 1254 is greater than the improvement threshold 1246. As such, processing circuitry 14 may determine that parameter plot 1238 indicates an improvement of a patient condition at day 6.

Although a magnitude of the worsening threshold 1242 and a magnitude of the improvement threshold 122 are illustrated as being substantially the same, in some examples, the magnitude of the worsening threshold 1242 and the magnitude of the improvement threshold 1246 may be different. That is, in some examples, a difference between the baseline parameter value 1244 and the worsening threshold 1242 may be different than a difference between the baseline parameter value 1244 and the improvement threshold 1246. In other examples, the difference between the baseline parameter value 1244 and the worsening threshold 1242 may be the same as the difference between the baseline parameter value 1244 and the improvement threshold 1246.

Figure 13:
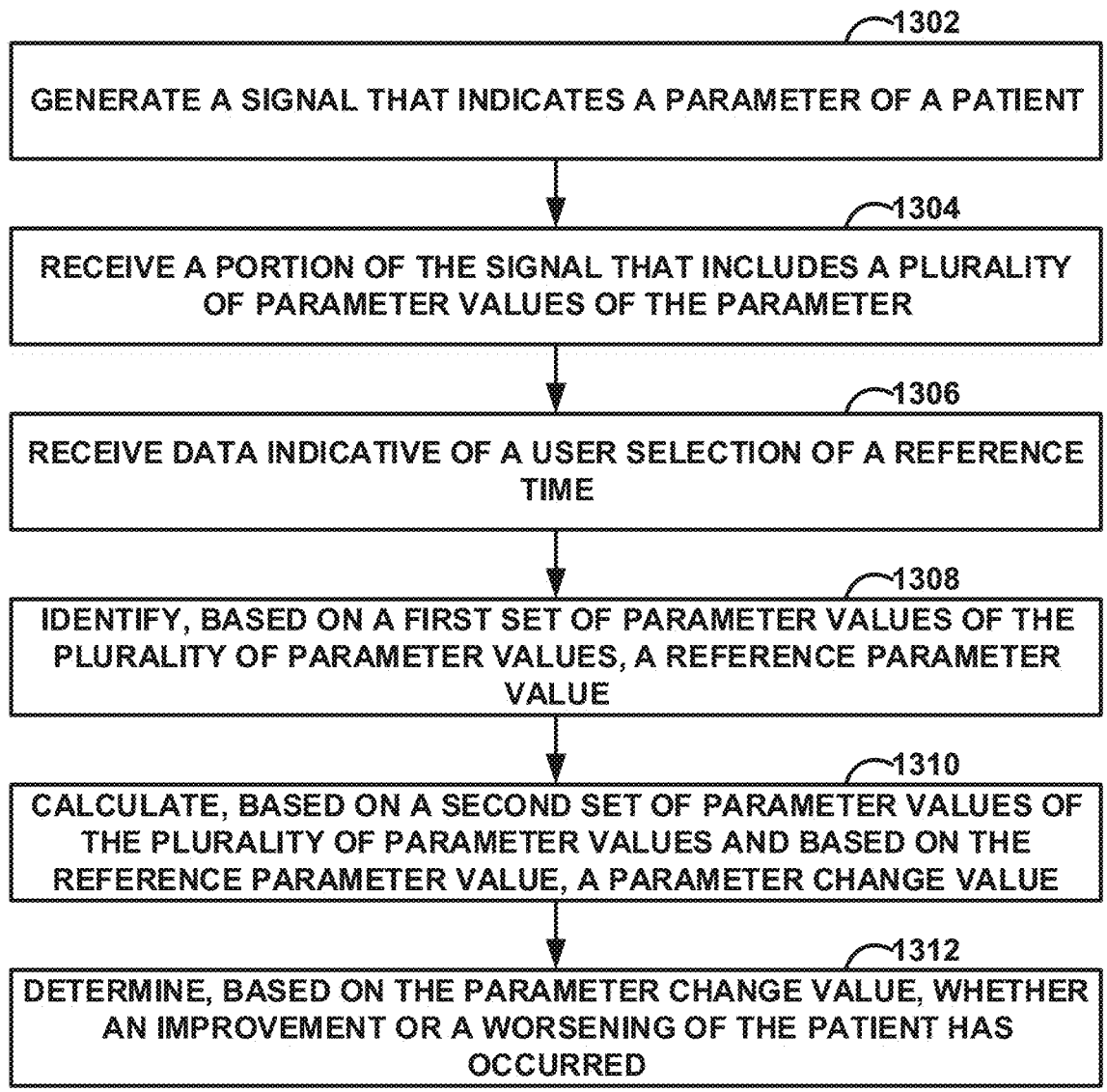
FIG. 13 is a flow diagram illustrating an example operation for determining whether an improvement or a worsening of one or more symptoms or physiological parameters has occurred in a patient based on a user selection of a reference time, in accordance with one or more techniques of this disclosure.

FIG. 13 is a flow diagram illustrating an example operation for determining whether an improvement or a worsening of one or more symptoms or physiological parameters has occurred in a patient based on a user selection of a reference time, in accordance with one or more techniques of this disclosure. FIG. 13 is described with respect to IMD 10, external device 12, and processing circuitry 14 of FIGS. 1-6. However, the techniques of FIG. 13 may be performed by different components of IMD 10, external device 12, and processing circuitry 14 or by additional or alternative medical device systems. Processing circuitry 14 is conceptually illustrated in FIG. 1 as separate from IMD 10 and external device 12 but may be processing circuitry of IMD 10 and/or processing circuitry of external device 12. In general, the techniques of this disclosure may be performed by processing circuitry 14 of one or more devices of a system, such as one or more devices that include sensors that provide signals, or processing circuitry of one or more devices that do not include sensors, but nevertheless analyze signals using the techniques described herein. For example, another external device (not pictured in FIG. 1) may include at least a portion of processing circuitry 14, the other external device configured for remote communication with IMD 10 and/or external device 12 via a network.

IMD 10 generates a signal that indicates a parameter of patient 4 (1302). In some examples, the parameter may include a subcutaneous impedance of patient 4, a respiratory rate of patient 4, a heart rate of patient 4, an AF burden of patient 4, or a ventricular rate of patient 4 while patient 4 is experiencing AF. Processing circuitry 14 receives a portion of the signal that includes the plurality of parameter values of the parameter (1304). In some examples, the plurality of parameter values may represent a sequence of parameter values which are collected by IMD 10 at a predetermined frequency, such as one parameter value per day, one parameter value per hour, or any other frequency.

Processing circuitry 14 may receive data indicative of a user selection or indication of a reference time (1306). In some examples, the reference time may represent a time in which a treatment program administered to patient 4 begins. Processing circuitry 14 may receive the data indicative of the user selection from IMD 10, external device 12, or another external device. Processing circuitry 14 may identify, based on a first set of parameter values of the plurality of parameter values, a reference parameter value (1308). In some examples, the first set of parameter values are collected by IMD 10 before the reference time. In some examples, processing circuitry 14 may calculate the reference parameter value to be a mean or a median of the first set of parameter values. Processing circuitry 14 may calculate, based on a second set of parameter values of the plurality of parameter values and based on the reference parameter value, a parameter change value (1310). Subsequently, processing circuitry 14 may determine, based on the parameter change value, whether an improvement or a worsening patient has occurred (1312).

Figure 14:
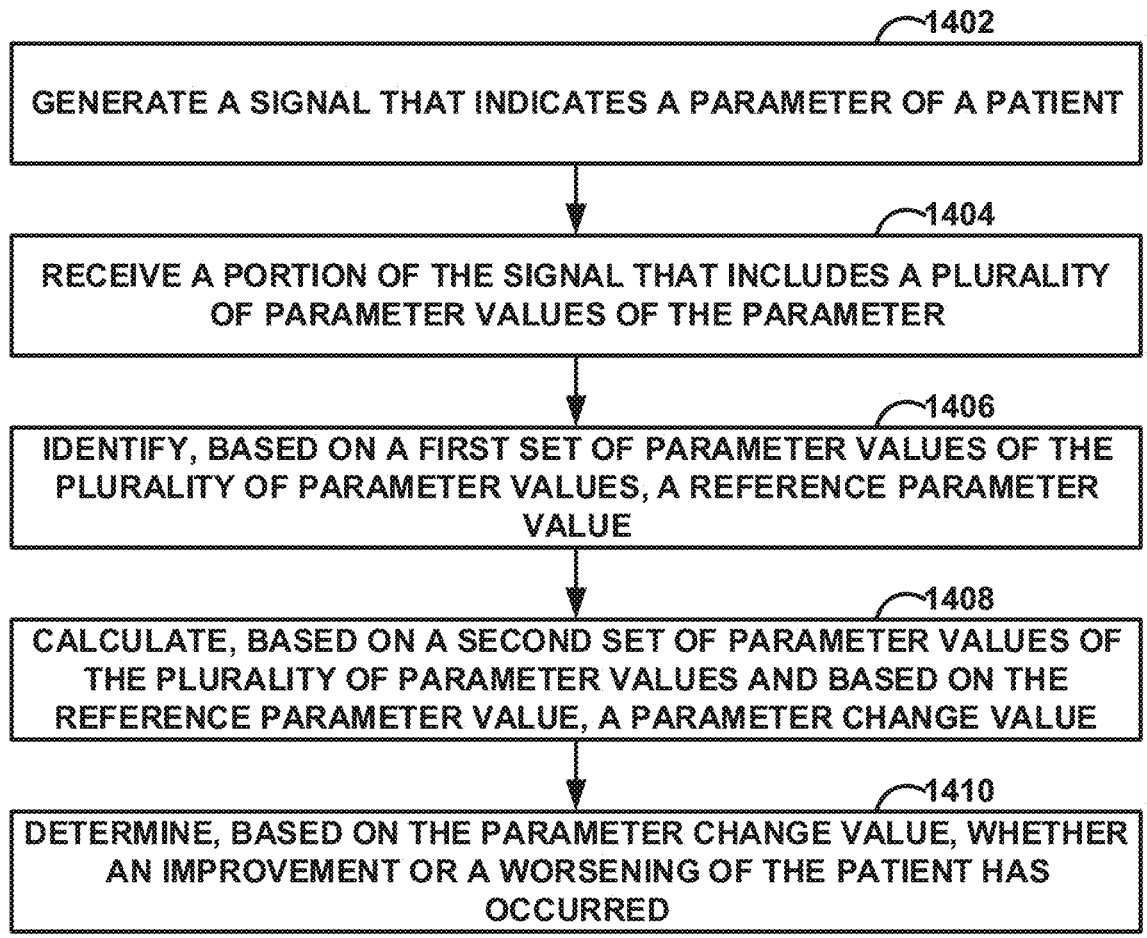
FIG. 14 is a flow diagram illustrating an example operation for determining whether an improvement or a worsening of one or more symptoms or physiological parameters has occurred in a patient based on a rolling window, in accordance with one or more techniques of this disclosure.

FIG. 14 is a flow diagram illustrating an example operation for determining whether an improvement or a worsening of one or more symptoms or physiological parameters has occurred in a patient based on a rolling window, in accordance with one or more techniques of this disclosure. FIG. 14 is described with respect to IMD 10, external device 12, and processing circuitry 14 of FIGS. 1-6. However, the techniques of FIG. 14 may be performed by different components of IMD 10, external device 12, and processing circuitry 14 or by additional or alternative medical device systems. Processing circuitry 14 is conceptually illustrated in FIG. 1 as separate from IMD 10 and external device 12 but may be processing circuitry of IMD 10 and/or processing circuitry of external device 12. In general, the techniques of this disclosure may be performed by processing circuitry 14 of one or more devices of a system, such as one or more devices that include sensors that provide signals, or processing circuitry of one or more devices that do not include sensors, but nevertheless analyze signals using the techniques described herein. For example, another external device (not pictured in FIG. 1) may include at least a portion of processing circuitry 14, the other external device configured for remote communication with IMD 10 and/or external device 12 via a network.

IMD 10 generates a signal that indicates a parameter of patient 4 (1402). In some examples, the parameter may include a subcutaneous impedance of patient 4, a respiratory rate of patient 4, a heart rate of patient 4, an AF burden of patient 4, or a ventricular rate of patient 4 while patient 4 is experiencing AF. Processing circuitry 14 receives a portion of the signal that includes the plurality of parameter values of the parameter (1404). In some examples, the plurality of parameter values may represent a sequence of parameter values which are collected by IMD 10 at a predetermined frequency, such as one parameter value per day, one parameter value per hour, or any other frequency.

Processing circuitry 14 may identify, based on a first set of parameter values of the plurality of parameter values, a reference parameter value (1406). In some examples, processing circuitry 14 may calculate the reference parameter value to be a mean, a median, or another statistical representation of the first set of parameter values. Processing circuitry 14 may calculate, based on a second set of parameter values of the plurality of parameter values and based on the reference parameter value, a parameter change value (1408). In some examples, processing circuitry 14 may select the first set of parameter values and the second set of parameters based on a rolling window. That is, the first set of parameter values and the second set of parameters update as time advances, and a predetermined number of parameter values separate the first set of parameter values and the second set of parameter values. Subsequently, processing circuitry 14 may determine, based on the parameter change value, whether an improvement or a worsening patient has occurred (1410).

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:
1. A medical device system comprising:
an implantable medical device comprising one or more sensors, wherein the implantable medical device is configured to be implanted underneath a skin of a patient so that the implantable medical device and the one or more sensors occupy a desired orientation over a period of time greater than seven days, wherein a length of the implantable medical device is greater than a depth of the implantable medical device and a width of the implantable medical device is greater than the depth of the implantable medical device so that the implantable medical device and the one or more sensors are configured to remain in the desired orientation following implantation throughout the period of time greater than seven days,
wherein the one or more sensors comprise:
sensing circuitry; and
a set of electrodes located on a first major surface of the implantable medical device opposite a second major surface of the implantable medical device, wherein the first major surface faces target tissue of the patient when the implantable medical device occupies the desired orientation over the period of time greater than seven days, and
wherein the sensing circuitry is configured to continuously generate, based on a physiological signal sensed from the target tissue via the set of electrodes, an electrical signal that indicates a parameter of the patient over the period of time greater than seven days; and
processing circuitry configured to:

receive data indicative of a user selection of a reference time indicating a start of a treatment;

determine a plurality of parameter values of the parameter based on a portion of the electrical signal corresponding to a time window including the reference time, wherein each parameter value of the plurality of parameter values represents a measurement of the parameter for a respective time interval during the time window;

identify, based on a first set of parameter values of the plurality of parameter values occurring before the reference time, a reference parameter value;

identify a set of difference values, wherein each difference value of the set of difference values represents a difference between the respective parameter value of a second set of parameter values and the reference parameter value, wherein the second set of parameter values occur after the reference time;

determine a sum of the set of difference values;

determine a delta value which represents a difference between the reference parameter value and a target parameter value;

calculate a parameter change value by determining a ratio of the sum of the set of difference values to the delta value;

determine, based on the parameter change value, whether an improvement or a worsening of the patient has occurred responsive to the treatment; and generate information indicating whether an improvement or a worsening of the patient has occurred responsive to the treatment.

2. The medical device system of claim 1, wherein to identify the reference parameter value, the processing circuitry is configured to calculate the reference parameter value to be a mean of the first set of parameter values.

3. The medical device system of claim 1, wherein to identify the reference parameter value, the processing circuitry is configured to calculate the reference parameter value to be a median of the first set of parameter values or another statistical representation of the first set of parameter values.

4. The medical device system of claim 1, wherein to determine whether the improvement or the worsening of the patient has occurred, the processing circuitry is configured to:

compare the parameter change value with a first threshold parameter change value and a second threshold parameter change value;

determine that the improvement of the patient has occurred when the parameter change value is greater than the first threshold parameter change value;

determine that the worsening of the patient has occurred when the parameter change value is less than the second threshold parameter change value; and determine that neither the improvement nor the worsening of the patient has occurred when the parameter change value is greater than or equal to the second threshold parameter change value and less than or equal to the first threshold parameter change value.

5. The medical device system of claim 4, wherein the first threshold parameter change value is within a range from 0.5 to 0.9.

6. The medical device system of claim 5, wherein the first threshold parameter change value is 0.7.

7. The medical device system of claim 1, wherein the plurality of parameter values represents a sequence of parameter values, and wherein the processing circuitry is configured to select the second set of parameter values to be consecutive parameter values of the sequence of parameter values starting a predetermined number of parameter values after the reference time.

8. The medical device system of claim 7, wherein the second set of parameter values comprises three consecutive parameter values, and wherein three parameter values separate the second set of parameter values and the reference time.

9. The medical device system of claim 1, wherein each parameter value of the plurality of parameter values corresponds to a respective time interval of a sequence of time intervals.

10. The medical device of claim 9, wherein each parameter value of the plurality of parameter values represents a set of parameter value components collected during the respective time interval, and wherein to determine the plurality of parameter values, the processing circuitry is configured to calculate each parameter value of the plurality of parameter values based on the respective set of parameter value components.

11. The medical device of claim 9, wherein the duration which defines each time interval of a sequence of time intervals is one day.

12. The medical device of claim 1, wherein the parameter is a first parameter, wherein the electrical signal is a first electrical signal, wherein the plurality of parameter values is a first plurality of parameter values, wherein the reference parameter value is a first reference parameter value, wherein the parameter change value is a first parameter change value, wherein the one or more sensors of the implantable medical device are configured to generate a second electrical signal that indicates a second parameter of the patient, wherein the one or more sensors are configured to continuously generate the second electrical signal that indicates the second parameter of the patient over the period of time greater than seven days, and wherein the processing circuitry is further configured to:

determine a second plurality of parameter values of the second parameter based on a portion of the second electrical signal corresponding to the time window including the reference time, wherein each parameter value of the second plurality of parameter values represents a measurement of the second parameter for a respective time interval during the time window;

identify, based on a third set of parameter values of the second plurality of parameter values occurring before the reference time, a second reference parameter value;

calculate, based on a fourth set of parameter values of the second plurality of parameter values occurring after the reference time and based on the second reference parameter value, a second parameter change value; and determine, based on the second parameter change value, whether the improvement or the worsening of the patient has occurred responsive to the treatment administered beginning at the reference time.

13. A method for controlling operation of a medical device system comprising:

generating, continuously by sensing circuitry of one or more sensors of an implantable medical device based on a physiological signal sensed from target tissue of a patient via a set of electrodes of the one or more sensors, an electrical signal that indicates a parameter of the patient over a period of time greater than seven days, wherein the implantable medical device is configured to be implanted underneath a skin of the patient so that the implantable medical device and the one or more sensors occupy a desired orientation over the period of time greater than seven days, wherein a length of the implantable medical device is greater than a depth of the implantable medical device and a width of the implantable medical device is greater than the depth of the implantable medical device so that the implantable medical device and the one or more sensors are configured to remain in the desired orientation following implantation throughout the period of time greater than seven days, wherein the set of electrodes are located on a first major surface of the implantable medical device opposite a second major surface of the implantable medical device, wherein the first major surface faces the target tissue of the patient when the implantable medical device occupies the desired orientation over the period of time greater than seven days;

receiving, by processing circuitry of the medical device system, data indicative of a user selection of a reference time indicating a start of a treatment;

determining, by the processing circuitry, a plurality of parameter values of the parameter based on a portion of the electrical signal corresponding to a time window including the reference time, wherein each parameter value of the plurality of parameter values represents a measurement of the parameter for a respective time interval during the time window;

identifying, by the processing circuitry based on a first set of parameter values of the plurality of parameter values occurring before the reference time, a reference parameter value;

identifying, by the processing circuitry, a set of difference values, wherein each difference value of the set of difference values represents a difference between the respective parameter value of a second set of parameter values and the reference parameter value, wherein the second set of parameter values occur after the reference time;

determining, by the processing circuitry, a sum of the set of difference values;

determining, by the processing circuitry, a delta value which represents a difference between the reference parameter value and a target parameter value;

calculating, by the processing circuitry, a parameter change value by determining a ratio of the sum of the set of difference values to the delta value;

determining, by the processing circuitry based on the parameter change value, whether an improvement or a worsening of the patient has occurred responsive to the treatment; and generating, by the processing circuitry, information indicating whether an improvement or a worsening of the patient has occurred responsive to the treatment.

14. The method of claim 13, wherein determining whether the improvement or the worsening of the patient has occurred comprises:

comparing the parameter change value with a first threshold parameter change value and a second threshold parameter change value;

determining that the improvement of the patient has occurred when the parameter change value is greater than the first threshold parameter change value;

determining that the worsening of the patient has occurred when the parameter change value is less than the second threshold parameter change value; and determining that neither the improvement nor the worsening of the patient has occurred when the parameter change value is greater than or equal to the second threshold parameter change value and less than or equal to the first threshold parameter change value.

15. The method of claim 13, wherein the parameter is a first parameter, wherein the electrical signal is a first electrical signal, wherein the plurality of parameter values is a first plurality of parameter values, wherein the reference parameter value is a first reference parameter value, wherein the parameter change value is a first parameter change value, wherein the method further comprises:

generating, by the one or more sensors of the implantable medical device, a second electrical signal that indicates a second parameter of the patient wherein the one or more sensors are configured to continuously generate the second electrical signal that indicates the second parameter of the patient over the period of time greater than seven days;

determining, by the processing circuitry, a second plurality of parameter values of the second parameter based on a portion of the second electrical signal corresponding to the time window including the reference time, wherein each parameter value of the second plurality of parameter values represents a measurement of the second parameter for a respective time interval during the time window;

identifying, by the processing circuitry based on a third set of parameter values of the second plurality of parameter values occurring before the reference time, a second reference parameter value;

calculating, by the processing circuitry based on a fourth set of parameter values of the second plurality of parameter values occurring after the reference time and based on the second reference parameter value, a second parameter change value; and determining, by the processing circuitry based on the second parameter change value, whether the improvement or the worsening of the patient has occurred responsive to the treatment administered beginning at the reference time.

16. A non-transitory computer-readable medium comprising instructions for causing one or more processors to:

control sensing circuitry of one or more sensors of an implantable medical device to generate, based on a physiological signal sensed from target tissue of a patient via a set of electrodes of the one or more sensors, an electrical signal that indicates a parameter of the patient over a period of time greater than seven days, wherein the implantable medical device is configured to be implanted underneath a skin of the patient so that the implantable medical device and the one or more sensors occupy a desired orientation over the period of time greater than seven days, wherein a length of the implantable medical device is greater than a depth of the implantable medical device and a width of the implantable medical device is greater than the depth of the implantable medical device so that the implantable medical device and the one or more sensors are configured to remain in the desired orientation following implantation throughout the period of time greater than seven days, wherein the set of electrodes are located on a first major surface of the implantable medical device opposite a second major surface of the implantable medical device, wherein the first major surface faces the target tissue of the patient when the implantable medical device occupies the desired orientation over the period of time greater than seven days;

receive data indicative of a user selection of a reference time;

determine a plurality of parameter values of the parameter based on a portion of the electrical signal corresponding to a time window including the reference time, wherein each parameter value of the plurality of parameter values represents a measurement of the parameter for a respective time interval during the time window;

identify, based on a first set of parameter values of the plurality of parameter values occurring before the reference time, a reference parameter value;

identify a set of difference values, wherein each difference value of the set of difference values represents a difference between the respective parameter value of a second set of parameter values and the reference parameter value, wherein the second set of parameter values occur after the reference time;

determine a sum of the set of difference values;

determine a delta value which represents a difference between the reference parameter value and a target parameter value;

calculate a parameter change value by determining a ratio of the sum of the set of difference values to the delta value;

determine, based on the parameter change value, whether an improvement or a worsening of the patient has occurred responsive to a treatment administered beginning at the reference time; and generate information indicating whether an improvement or a worsening of the patient has occurred responsive to the treatment.

17. The medical device system of claim 1, wherein the length of the implantable medical device being greater than the depth of the implantable medical device and the width of the medical device being greater than the depth of the implantable medical device prevents, throughout the extended period of time greater than seven days, the implantable medical device and the one or more sensors from transitioning from the desired orientation to an undesired orientation.

18. The medical device of claim 1,
wherein when the implantable medical device occupies the desired orientation, the first major surface faces outwards towards the skin of the patient and the second major surface faces inward toward musculature of the patient.

19. The medical device system of claim 1, wherein the electrical signal is a first electrical signal, wherein the parameter is a first parameter, wherein the plurality of parameter values is a first plurality of parameter values,
wherein the one or more sensors are configured to generate a second electrical signal that indicates a second parameter of the patient, and
wherein to determine whether an improvement or a worsening of the patient has occurred responsive to the treatment, the processing circuitry is configured to:
determine a second plurality of parameter values of the second parameter based on a portion of the second electrical signal corresponding to a period of time including the reference time;
determine whether the second plurality of parameter values indicate a change in patient motion or a change in patient posture; and
determine, based on the second plurality of parameter values indicating the change in patient motion or the change in patient posture, whether the parameter change value corresponding to the first parameter is attributable to the change in patient motion or the change in patient posture.

* * * * *